(12) United States Patent
Pitorre et al.

(10) Patent No.: US 12,186,433 B2
(45) Date of Patent: Jan. 7, 2025

(54) NANOCAPSULES COMPRISING MODIFIED NUCLEOBASES AND/OR NUCLEOSIDES, HYDROGELS AND OLEOGELS COMPRISING THEM AND USES THEREOF

(71) Applicants: UNIVERSITE D'ANGERS, Angers (FR); INSTITUT NATIONAL DE LA SANTE ET DE LA RECHERCHE MEDICALE (INSERM), Paris (FR); CENTRE NATIONAL DE LA RECHERCHE SCIENTIFIQUE, Paris (FR); CENTRE HOSPITALIER UNIVERSITAIRE D'ANGERS, Angers (FR)

(72) Inventors: Marion Pitorre, Angers (FR); Guillaume Bastiat, Briollay (FR); Jérôme Bejaud, Angers (FR); Jean-Pierre Benoit, Angers (FR)

(73) Assignees: Universite D'Angers France, Angers (FR); Institut National De La Sante et de la Recherche Medicale (INSERM), Paris (FR); Centre National de la Recherche Scientifique, Paris (FR); Centre Hospitalier Universitaire D'Angers Cedex France, Angers (FR)

( * ) Notice: Subject to any disclaimer, the term of this patent is extended or adjusted under 35 U.S.C. 154(b) by 356 days.

(21) Appl. No.: 16/644,275

(22) PCT Filed: Sep. 7, 2018

(86) PCT No.: PCT/EP2018/074221
§ 371 (c)(1),
(2) Date: Mar. 4, 2020

(87) PCT Pub. No.: WO2019/048649
PCT Pub. Date: Mar. 14, 2019

(65) Prior Publication Data
US 2021/0161828 A1 Jun. 3, 2021

(30) Foreign Application Priority Data
Sep. 8, 2017 (EP) .................................. 17306164

(51) Int. Cl.
*A61K 9/51* (2006.01)
*A61K 9/00* (2006.01)
(Continued)

(52) U.S. Cl.
CPC .......... *A61K 9/5123* (2013.01); *A61K 9/0019* (2013.01); *A61K 9/06* (2013.01); *C07H 19/06* (2013.01); *C07H 19/16* (2013.01)

(58) Field of Classification Search
CPC .............................. C07H 19/06; C07H 19/16
See application file for complete search history.

(56) References Cited

U.S. PATENT DOCUMENTS

| | | | |
|---|---|---|---|
| 8,057,823 B2 | 11/2011 | Heurtault et al. | |
| 2003/0152635 A1 | 8/2003 | Heurtault et al. | |

(Continued)

FOREIGN PATENT DOCUMENTS

| | | |
|---|---|---|
| CN | 107216362 | 9/2017 |
| EP | 2 883 959 A1 | 6/2015 |

(Continued)

OTHER PUBLICATIONS

International Search Report for PCT/EP2018/074221, Jan. 30, 2019, European Patent Office, Rijswijk, NL.
(Continued)

*Primary Examiner* — Benjamin J Packard
(74) *Attorney, Agent, or Firm* — B. Aaron Schulman, Esq.; Stites & Harbison, PLLC

(57) ABSTRACT

The present invention concerns modified nucleobases, nucleosides, deoxynucleosides, and/or their derivatives, nanocapsules comprising them, hydrogels and oleogels (Continued)

comprising said nanocapsules or said above-mentioned compounds and their uses, in particular their pharmaceutical uses.

11 Claims, 17 Drawing Sheets

(51) Int. Cl.
    *A61K 9/06*     (2006.01)
    *C07H 19/06*     (2006.01)
    *C07H 19/16*     (2006.01)

(56) References Cited

U.S. PATENT DOCUMENTS

2009/0238865 A1     9/2009    Heurtault et al.
2015/0141959 A1*   5/2015    Seward ............ A61M 25/0084
                                                                                                                                             604/508

FOREIGN PATENT DOCUMENTS

GB        1 297 398      11/1972
GB        1 449 708       9/1976

OTHER PUBLICATIONS

Written Opinion for PCT/EP2018/074221, Jan. 30, 2019, European Patent Office , Rijswijk, NL.

Marion Pitorre et al., "The design of hydrogels and organogels using the same nucleoside crosslinking agent", European Nanomedicine Meeting 2015—SFNANO, At Grenoble, France, XP055456476.

K. J. Skilling et al, "Gelation properties of self-assembling N-acyl modified cytidine derivatives", *Journal of Materials Chemistry B*, vol. 2, No. 47, Jan. 1, 2014 (Jan. 1, 2014), p. 8412-8417, XP055176082 DOI: 10.1039/C4TB01375A ISSN:2050-750X.

Sasso Maria Stella et al, "Low dose gemcitabine-loaded lipid nanocapsules target monocytic myeloid-derived suppressor cells and potentiate cancer immunotherapy", *Biomaterials, Elsevier Science Publishers BV., Barking, GB*, vol. 96, Apr. 22, 2016 (Apr. 22, 2016), p. 47-62, XP029541024 DOI: 10.1016/J.BIOMATERIALS. 2016.04.010 ISSN:0142-9612.

Jesse Pulido et al, "Synthesis and Cytostatic Evaluation of 4-N-Alkanoyl and 4-N-Alkyl Gemcitabine Analogues", *Journal of Medicinal Chemistry*, vol. 57, No. 1, Dec. 30, 2013 (Dec. 30, 2013), p. 191-203, XP055456311 DOI: 10.1021/jm401586a ISSN:0022-2623.

Maria Galini Faidra Angelerou et al, "Surface-directed modulation of supramolecular gel properties", *Chemical Communications*, vol. 52, No. 23, Jan. 1, 2016 (Jan. 1, 2016 ), p. 4298-4300, XP055456324 DOI: 10.1039/C6CC00292G ISSN:1359-7345.

Nathalie Wauthoz et al, "Safe lipid nanocapsule-based gel technology to target lymph nodes and combat mediastinal metastases from an orthotopic non-small-cell lung cancer model in SCID-CB17 mice", *Nanomedicine: Nanotechnology, Biology and Medicine*, vol. 11, No. 5, Jul. 1, 2015 (Jul. 1, 2015), p. 1237-1245, XP055456300 DOI: 10.1016/j.nano.2015.02.010 ISSN:1549-9634.

Colautti A et al, "Potential antivirals. XV. Pyrimidine and purine acyl derivatives", *Farmaco, Edizione Scientifica, Societa Chimica Italiana, Pavia, IT*, vol. 26, No. 8, Jan. 1, 1971 (Jan. 1, 1971), p. 710-717, XP009506083 ISSN:0430-0920.

European Search Report for Application No. EP17306164, Jul. 4, 2018, European Patent Office Munich.

* cited by examiner

NANOCAPSULES COMPRISING MODIFIED NUCLEOBASES AND/OR NUCLEOSIDES, HYDROGELS AND OLEOGELS COMPRISING THEM AND USES THEREOF

The present invention concerns modified nucleobases, nucleosides, deoxynucleosides, and/or their derivatives, nanocapsules comprising them, hydrogels and oleogels comprising said nanocapsules or said above-mentioned compounds and their uses, in particular their pharmaceutical uses.

In the field of pharmaceutical formulation, gel-like systems have received considerable attention for the development of new drug delivery systems. Coupling gel-like systems and nanoparticles appears to be promising to provide such new drug delivery systems.

For example, nanoparticles-based hydrogels have been made with liposomes, solid lipid nanoparticles, and micelles. Nevertheless, all these nanoparticles-based gelified systems have been obtained by adding synthetic or natural polymers in the formulation to induce gelation (i.e. gelling agents). In these gel-based systems, the polymers alone lead to gel formation and the nanoparticles are dispersed in the polymeric matrix, without any interaction with the tridimensional polymeric network. The nanoparticles are then released by diffusion or by erosion of the gel.

It is of great interest to limit the addition of excipients such as polymers in formulations, especially in pharmaceutical formulations, to avoid additional side effects and to simplify compositions. Pharmaceutical compositions with a limited number of excipients may lead to safer drug delivery systems, in particular in the treatment of cancers. Indeed, conventional chemotherapy is mainly delivered by perfusion which includes major limitations such as high systemic toxicity.

Therefore, there is a need for new, efficient, safe and easy-to-use drug delivery systems. More specifically, there is a need for locally delivered and/or sustained release formulations of active ingredients in form of gels.

In particular, there is a need for nanoparticles-based gels formulations with a limited number of excipients, preferably without the addition of polymers. There is also a need for safe and easy-to-use formulations to be used in the treatment of cancers and/or in the prevention and/or treatment of vascular diseases.

The aim of the present invention is to provide modified nucleobases, nucleosides, deoxynucleosides, and/or their derivatives, in particular useful as gelling agents in the preparation of hydrogels and/or oleogels.

Another aim of the invention is to provide nanocapsules, in particular useful in the preparation of hydrogels and/or oleogels, preferably hydrogels.

Another aim of the invention is to provide hydrogels and/or oleogels obtained without the addition of a further gelling agent such as a polymer.

An aim of the invention is to provide a drug delivery system which is safe, ready-to-use and adapted to various active ingredients, either lipophilic or hydrophilic.

An aim of the invention is to provide a drug delivery system in the form of a hydrogel or oleogel which allow the local deposit and/or the sustained release of active ingredients.

An aim of the invention is to provide a drug delivery system useful in the treatment of cancers and/or in the prevention and/or treatment of vascular diseases.

The invention thus relates to a compound A having the following formula (A):

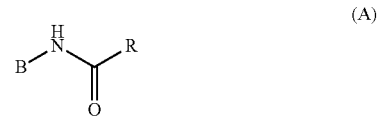

wherein:
B is selected from the group consisting of a nucleobase, a nucleoside, a deoxynucleoside, and one of their derivatives, and
R is selected from linear or branched, saturated or unsaturated $(C_9-C_{21})$alkyl, said alkyl group being optionally substituted by one or more substituent(s) selected from the group consisting of:
—COOH, —OH, —SH, —NH$_2$, —COORa, —ORa, —SRa, and —NRaRb,
with Ra being a linear or branched, saturated or unsaturated $(C_1-C_{10})$alkyl, and
Rb being H or a linear or branched, saturated or unsaturated $(C_1-C_{10})$alkyl,
provided that said compound A is not:

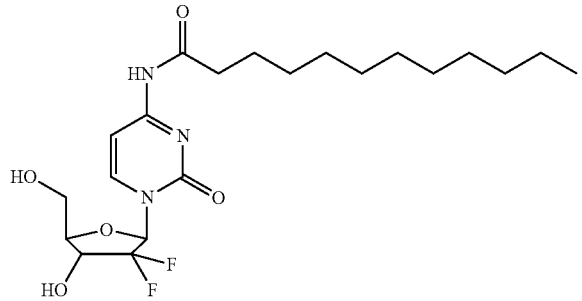 [SMILES: CCCCCCCCCCCC(=O)Nc1ccn(C2OC(CO)C(O)C2(F)F)c(=O)n1]

The excluded compound corresponds to a compound A, wherein in formula (A), B is gemcitabine and R is a linear saturated alkyl having 11 carbon atoms, not substituted.

The present invention also relates to a hydrogel or oleogel for its use in a method for the treatment and/or prevention of vascular diseases, such as vascular hyperplasia, and cancers,
wherein said hydrogel comprises nanocapsules and an aqueous phase, and has a G"/G' inferior to 1, preferably comprised between 0.1 and 0.5,
said nanocapsules comprising at least one compound A and having a mean size diameter of less than 150 nm,
wherein said oleogel comprises at least one compound A and an oily phase, said oleogel having a G"/G' ratio inferior to 1, preferably comprised between 0.1 and 0.5,
and wherein said compound A having the formula (A).

Surprisingly, the inventors discovered that the compounds of formula (A) allow the spontaneous formation of hydrogels and/or oleogels.

Indeed, a hydrogel according to the invention is formed spontaneously when nanocapsules (also called lipid nanocapsules or LNCs) comprising said compounds of formula (A) are put in contact with an aqueous phase. In a similar way, an oleogel according to the invention is formed spontaneously when said compounds of formula (A) are put in contact with an oily phase.

Without being bond to a theory, it has been shown that the compounds of formula (A) are localized at the oil-in-water interface between the nanocapsules and the aqueous medium and that they are exposed to water (i.e. they are in the external side of the shell of the nanocapsules). This particular assembly promotes inter-nanocapsules interactions via hydrogen bonds between the compounds of formula (A), that leads to a nanocapsules-based hydrogel structure. This interaction between the compounds of formula (A) via hydrogen bonds is also obtained when said compounds are put in an oily phase, leading to the formation of an oleogel. The hydrogel and oleogel of the invention are thus obtained without the use of a further gelling agent such as a polymer.

Even more stricking, dilution of the hydrogel in water produces a suspension of the nanocapsules in water from which nanocapsules can be easily recovered.

By contrast with the already known gel-like systems, the hydrogel of the invention does not leave any residues, for example a polymeric matrix or polymeric residues, once it is placed in a biological medium to release the active ingredients contained in it.

Advantageously, the hydrogel and/or oleogel of the invention allow the delivery of hydrophilic and/or lipophilic active ingredients, especially anticancer drugs.

Such gelified formulations are also particularly adapted to the local administration by syringes and can be easily used in therapeutic applications that need the local administration and/or the sustained release of active ingredients, such as in the treatment of cancers and/or in the prevention and/or treatment of vascular diseases.

Definitions

The term "alkyl" means a saturated or unsaturated aliphatic hydrocarbon group which may be straight or branched. For example, it can be cited the methyl, ethyl, propyl, isopropyl, ethylene or propylene group. "Branched" means that one or lower alkyl groups such as methyl, ethyl or propyl are attached to a linear alkyl chain.

By "nucleobase" is meant adenine (A), cytosine (C), guanine (G), thymine (T), and uracil (U); preferably adenine, cytosine and guanine.

By "nucleoside" is meant a nucleobase as defined above, linked to a ribose. By "deoxynucleoside" is meant a nucleobase as defined above, linked to a deoxyribose.

By "gelling agent", it may be meant any component or excipient which forms a gel when added to and mixed with a liquid composition. In particular, a gelling agent increases the viscosity of a liquid composition to give a gel. Gelling agents are usually synthetic or natural polymers. As gelling agents, it may be cited polysaccharides such as starches, vegetable gums or pectins; carboxymethylcellulose; gelatin or synthetic polymers such as pluronic, poly-N-isopropylacrylamide or polycaprolactone. In particular, the compounds of formula (A) of the invention may be considered as gelling agents (or reticulating agents) when used according to the invention. It may be understood that the hydrogel and/or oleogel of the invention only comprise the compounds of formula (A) as gelling agents and no further gelling agents.

By "hydrogel", it may be understood a semi-solid formulation, preferably composed of a tridimensional network of nanocapsules (i.e. self-assembled nanocapsules) of the invention immersed in an aqueous phase and retaining it. In one embodiment, said hydrogel is semi-solid at a temperature comprised between 15° C. and 80° C.

By "oleogel", it may be understood a semi-solid formulation, preferably composed of a tridimensional network of compounds of formula (A) (i.e. self-assembled compounds) of the invention immersed in an oily phase and retaining it.

The hydrogel and/or oleogel according to the invention may be characterized by their elastic modulus (G') and/or their viscous modulus (G") and/or their G"/G' ratios. These parameters are well-known in the field of gels and are defined for example in the handbook "Initiation à la rhéologie. Bases théoriques et applications expérimentales" (4° Éd., Lavoisier, 2014) by Couarraze G., Grossiord J-L, and Huang N. The elastic modulus (also known as storage modulus) is a value that measures the material's elasticity: a non-permanent deformation when a stress is applied to it. The viscous modulus (also known as loss modulus) is a value that is characteristic of the material's flowing: a permanent deformation, when a stress is applied to it.

The viscoelastic properties (elastic (G') and viscous (G") moduli) of the hydrogels and the oleogels can be measured using a rheometer such as Kinexus® apparatus (Malvern Instruments S.A, Worcestershire, Royaume-Uni). The values of G' and G" moduli may be determined in the range of oscillation frequency from 0.1 to 10 Hz, at constant shear strain (in the linear regime).

Compounds of General Formula (I)

In a particular embodiment, the compounds having the following formula (D) are excluded from the present invention:

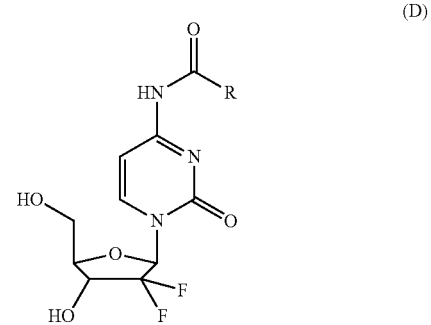

(D)

wherein R is as defined herein.

In one embodiment, the compound A has one of the following formulae:

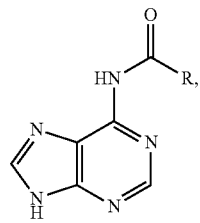

(a)

(b) 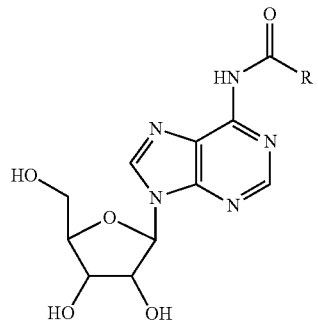

(c) 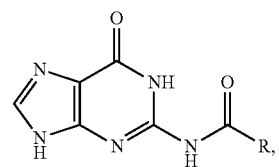

(d) 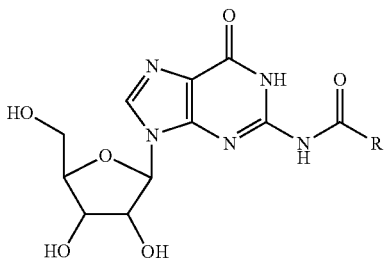

(e) 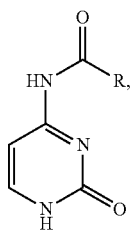

(f) 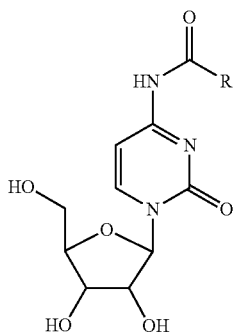

(g) 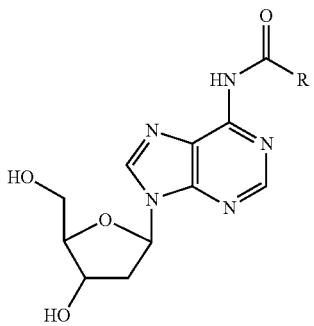

(h) 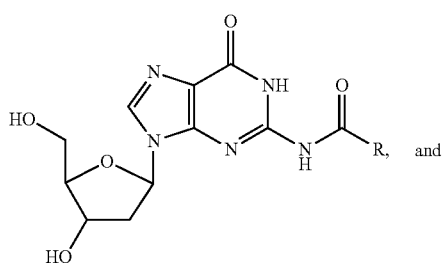

and (i) 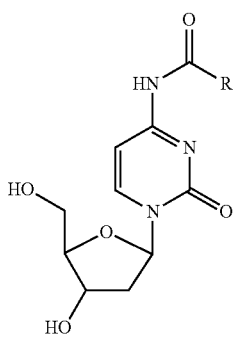

with R being as defined herein.

In one embodiment, B is selected from the group consisting of a nucleobase, a nucleoside and a deoxynucleoside.

By "a derivative of a nucleobase, a nucleoside or a deoxynucleoside", it may be meant a methylated and/or halogenated nucleobase, nucleoside or deoxynucleoside respectively such as 5-methylcytidine or 7-methylguanosine.

In one embodiment, R is selected from linear or branched, saturated or unsaturated $(C_{10}$-$C_{20})$alkyl, said alkyl group being optionally substituted by one or more substituent(s), preferably by one or two substituent(s) such as defined above.

In one embodiment Ra is a saturated $(C_1$-$C_5)$alkyl and/or Rb is H or a saturated $(C_1$-$C_5)$alkyl, preferably, Ra is a methyl, ethyl, propyl or isopropyl group and Rb is H or a methyl, ethyl, propyl or isopropyl group. In one embodiment Ra and Rb are a saturated $(C_1$-$C_5)$alkyl, preferably chosen among the methyl, ethyl, propyl and isopropyl groups.

In one embodiment, R is linear. In another embodiment, R is not substituted. In particular, R is a linear alkyl having 9, 11, 13, 15, 17, 19, or 21 carbon atoms, preferably 15 carbon atoms. In a particular embodiment, when R is unsaturated, it comprises one or two double bonds, preferably one double bond. In one embodiment, when B is a cytidine, then R comprises at least 13 carbon atoms.

In one embodiment, R is selected from the group consisting of: —(CH$_2$)$_{10}$—CH$_3$, —(CH$_2$)$_{12}$—CH$_3$, —(CH$_2$)$_{14}$—CH$_3$, —(CH$_2$)$_{16}$—CH$_3$ and (CH$_2$)$_7$—CH═CH—(CH$_2$)$_7$—CH$_3$.
In one embodiment, said compound A has one of the following formulae:
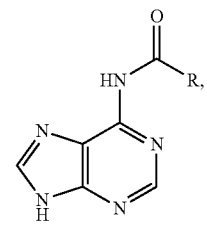
(a)
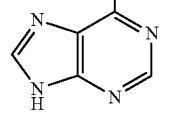
(c)
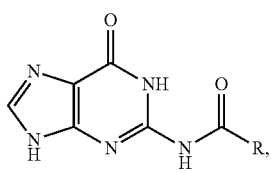
(e)
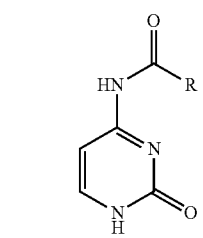
R being as defined above.
In another embodiment, said compound A has one of the following formulae:
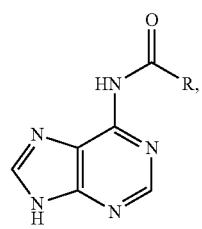
(a)
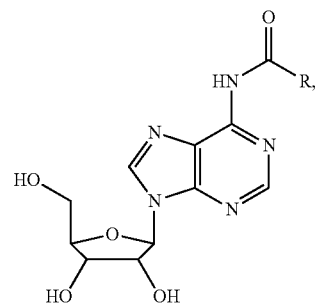
(b)
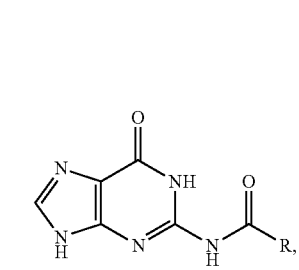
(c)
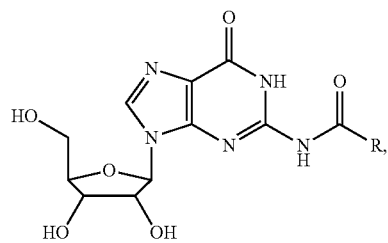
(d)
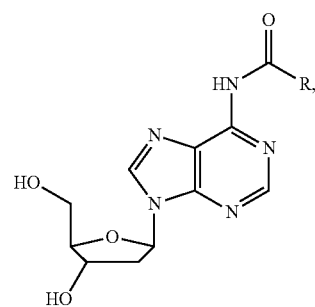
(g)
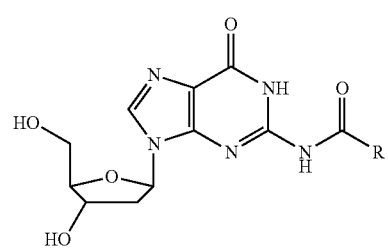
(h)
R being as defined above.

In another embodiment, said compound A has one of the following formulae:
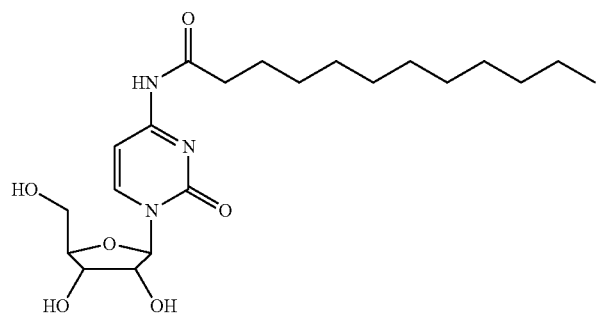
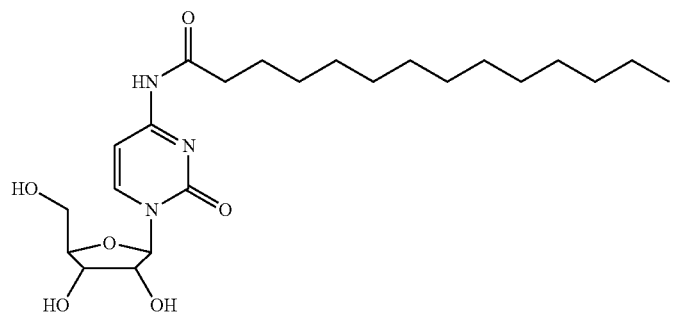
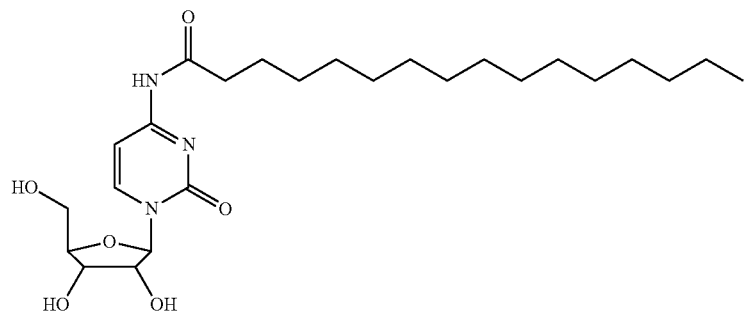 [SMILES: CCCCCCCCCCCCCCCC(=O)Nc1ccn(C2OC(CO)C(O)C2O)c(=O)n1]
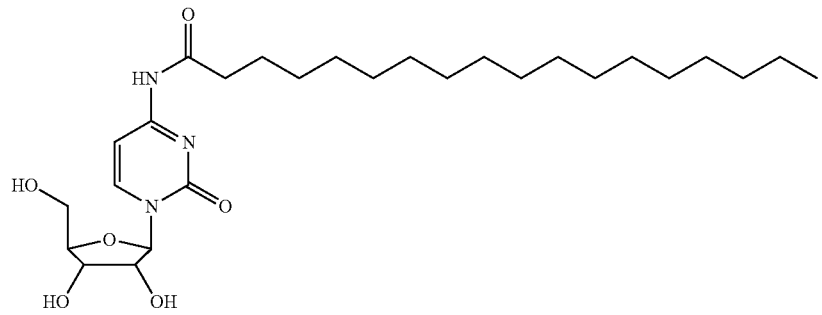
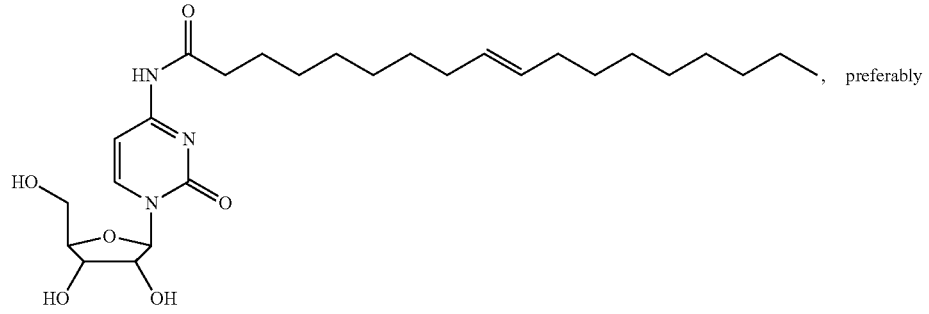, preferably

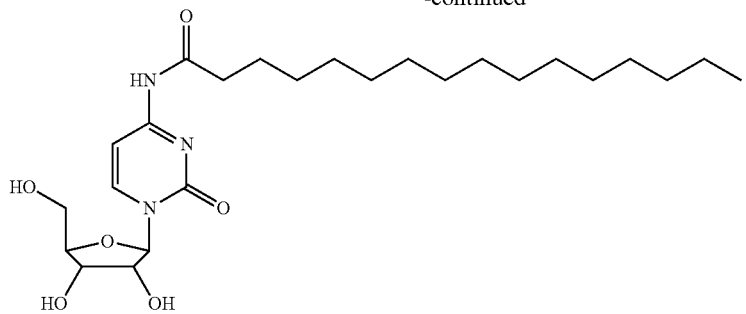

Nanocapsules

The present invention also relates to a nanocapsule comprising at least one compound A as defined above, having a mean size diameter of less than 150 nm.

The nanoparticles according to the invention and their process of preparation are also described in the international patent application WO 01/64328 (from page 3, 1.29 to page 5, 1.14).

More particularly, the mean size diameter of the nanocapsules of the invention is comprised between 20 nm and 115 nm, preferably between 25 nm and 100 nm, even more preferably between 50 nm and 100 nm, for example between 40 nm and 110 nm. For example the mean size diameter of the nanocapsules of the invention is of about 25, 50, 75 and 100 nm.

In one embodiment, said nanocapsule has a core/shell structure wherein said core comprises a fatty phase and wherein said shell comprises at least one surfactant. In one embodiment said core is liquid or semi-liquid at ambient temperature and said shell is solid at ambient temperature. By "ambient temperature" is meant a temperature comprised between 15° C. and 25° C.

In a particular embodiment, said fatty phase is selected from the group consisting of: triglycerides, diglycerides, monoglycerides and their mixtures, preferably triglycerides.

In one embodiment, the triglycerides, diglycerides, or monoglycerides contain fatty acids having from 8 to 22 carbon atoms. In a particular embodiment, the fatty phase consists of a mixture of capric acid and caprylic acid triglycerides, for example commercialized as Labrafac® WL 1349.

In one embodiment, the shell of the nanocapsule comprises at least one lipophilic surfactant such as phospholipids (such as lecithines) or monoalkylated sorbitans, and may further comprise at least one hydrophilic surfactant such as PEG derivatives surfactants, preferably non-ionic. In one embodiment, the HLB of said lipophilic surfactant is comprised between 2 and 7. In another embodiment, the HLB of the hydrophilic surfactant is comprised between 10 and 20, preferably between 10 and 17. In a particular embodiment, the shell consists of a mixture of Span® 80 and Kolliphor® HS15.

In one embodiment, the ratio surfactant(s)/(surfactant(s)+ fatty phase) is comprised between 0.4 and 0.8 (w/w). In another embodiment, the ratio compound A/fatty phase is comprised between 0.01 and 0.1 (w/w).

In a particular embodiment, the nanocapsules of the invention comprise:
- a shell, comprising the compounds A of the invention, Span® 80 and Kolliphor® HS15; and
- a core comprising Labrafac® WL 1349 and optionally an active ingredient M as defined below.

In one embodiment, the zeta potential of the nanocapsules according to the invention is inferior to −2 mV, for example comprised between −2 mV and −4 mv. In one embodiment, the nanocapsules of the invention have a polydispersity index of less than 0.1, for example comprised between 0.04 and 0.9, thus demonstrating their monodisperse and monomodal distribution.

Preferably, the nanocapsule of the invention further comprises an active ingredient M in the core of the nanocapsule. In one embodiment, said active ingredient M is lipophilic or amphipilic.

In one embodiment, said active ingredient M is lipophilic or amphiphilic and is selected among:
- chemotherapeutic agents;
- anti-parasitic agents, more particularly anti-helminthic agents such as ivermectin, albendazole, praziquantel, benznidazole and fenbendazole.
- antiarrhythmic agents such as amiodarone; and
- anticoagulant agents such as fondaparinux.

Among chemotherapeutic agents, it can be cited the taxdids such as paclitaxel, and docetaxel; tamoxifene or its derivatives; ferrociphenes such as ferrociphenol; camptothecine and its analogues such as irinotecan and Sn38; and etoposide.

In a particular embodiment, said active ingredient M is a chemotherapeutic agent, such as a cytotoxic or a cytostatic compound, for example a taxdid and preferably paclitaxel.

In a particular embodiment, said active ingredient M is chosen from the group consisting of:
- antimitotic agents such as paclitaxel, docetaxel, vincristine, and vinblastine;
- alkylating agents such as melphalan;
- intercalant agents such as amsacrine;
- antimetabolic agents such as methotrexate, aliphatic modified gemcitabine.

According to the invention, said active ingredient M is different from compound A.

Hydrogel

The invention relates to a hydrogel comprising nanocapsules as defined above and an aqueous phase, said hydrogel having a G"/G' ratio inferior to 1, preferably inferior or equal to 0.5 and more preferably comprised between 0.1 and 0.5. In one embodiment, the hydrogel according to the invention consists of nanocapsules as defined above and an aqueous phase. In one embodiment, said hydrogel does not comprise a gelling agent which is different from the compounds of formula (A).

In one embodiment, said hydrogel has a transition gel-LNC suspension temperature comprised between 25° C. and 100° C., preferably between 40° C. and 70° C.

In one embodiment, the G" value of the hydrogel is comprised between 0.5 and 5 000 Pa. In another embodiment, the G' value of the hydrogel is comprised between 5 and 10 000 Pa.

In a particular embodiment, said aqueous phase is chosen from the group consisting of: water, water for injection (WFI), 0.9% sodium chloride solution for injection, and aqueous buffers.

In another embodiment, the ratio (surfactant(s)+fatty phase)/(surfactant(s)+fatty phase+aqueous phase) is comprised between 0.01 and 0.5 (w/w).

Preferably, the hydrogel of the invention further comprises an active ingredient N, in the aqueous phase of the hydrogel. In one embodiment, said active ingredient N is hydrophilic. In a particular embodiment, said active ingredient N is chosen from the group consisting of: peptides; proteins; antibodies; bio-similars; siRNA; alkylating agents such as cisplatine, lomustine; intercalant agents such as doxorubicine, epirubicine; antimetabolic agents such as gemcitabine, decitabine, 5-fluorouracile, cytarabine; and enzymatic inhibitors such as rivastigmine.

The present invention also relates to a process for preparing a hydrogel as defined above, comprising a step of adding an aqueous phase to nanocapsules as defined above.

Oleogel

The present invention relates to an oleogel comprising at least one compound A as defined above and an oily phase, said oleogel having a G"/G' ratio inferior to 1, preferably inferior or equal to 0.5 and more preferably comprised between 0.1 and 0.5.

In one embodiment, the oleogel according to the invention consists of compounds of formula (A) as defined above and an oily phase. In one embodiment, said oleogel does not comprise a gelling agent which is different from the compounds of formula (A).

In one embodiment, the oleogel has a transition gel-LNC suspension temperature comprised between 25° C. and 100° C., preferably between 40° C. and 70° C.

In one embodiment, the G" value of the hydrogel is comprised between 0.5 and 500 000 Pa. In another embodiment, the G' value of the hydrogel is comprised between 5 and 1 000 000 Pa. In one embodiment, the ratio compounds A/oily phase is comprised between 0.005 and 0.2 (w/w).

In one embodiment, said oily phase is selected from the group consisting of: triglycerides, diglycerides, monoglycerides and their mixtures. In one embodiment, said oily phase consists of triglycerides, diglycerides, monoglycerides or their mixtures, preferably triglycerides. In one embodiment, the triglycerides, diglycerides, or monoglycerides contain fatty acids having from 8 to 22 carbon atoms. In a particular embodiment, the oily phase consists of a mixture of capric acid and caprylic acid triglycerides (for example commercialized as Labrafac® WL 1349).

Preferably, the oleogel of the invention further comprises an active ingredient P, said active ingredient P being in the oily phase of the oleogel. In one embodiment, said active ingredient P is hydrophilic or lipophilic. In a particular embodiment, said active ingredient P is chosen in the list of active ingredients M or active ingredients N as defined above.

The present invention also relates to a process for preparing an oleogel as defined above, comprising a step of adding an oily phase to compounds (A) as defined above.

In a particular embodiment, the process for preparing an oleogel comprises the following steps:
c) solubilizing the compounds A, and optionally the active ingredient P if it is lipophilic, in the oily phase, at a temperature comprised between 50° C. and 100° C., for example around 70° C.;
d) optionally adding an hydrophilic active ingredient P in the obtained oily phase; cooling the oily phase obtained in step a) or b), preferably to a temperature comprised between 4° C. and 25° C., thereby obtaining an oleogel.

Pharmaceutical Uses

In one embodiment, the hydrogel and/or the oleogel according to the invention is(are) biodegradable. In one embodiment, the hydrogel and/or the oleogel of the invention is(are) administered locally and/or is(are) a sustained release drug delivery system.

The invention also relates to the hydrogel and/or the oleogel as defined above, for use in the prevention and/or treatment of vascular diseases, such as vascular hyperplasia, and cancers. The invention also relates to the hydrogel and/or the oleogel as defined above, for use in a method for the treatment and/or prevention of vascular diseases, such as vascular hyperplasia, and cancers. In one embodiment, said hydrogel or oleogel is administered locally and/or is a sustained release drug delivery system.

By the term "cancer" is meant solid tumors and/or disseminated hematological cancers and/or their metastasis. The terms "metastasis" or "metastatic diseases" refer to secondary tumors that are formed by cells from a primary tumor which have moved to another localization. The term "hematological cancers" refers to types of cancer that affect blood, bone marrow, and lymph nodes such as myelomas, lymphomas or leukemias.

In one embodiment, said cancer is selected from the group consisting of: pancreatic cancer, lung cancer, non-small cells lung cancer, breast cancer, bladder cancer, melanoma, leukemia and brain cancer such as glioblastoma.

More particularly, the hydrogel and/or the oleogel as defined above (is)are intended for use in the treatment of cancers after the resection of a solid tumor or by intratumoral administration.

The invention relates to the hydrogel as defined above and/or the oleogel as defined above, for use in the prevention and/or treatment of vascular diseases such as vascular hyperplasia, more particularly intimal hyperplasia. In a particular embodiment, said use follows or replaces stent implantation, in prevention of intimal hyperplasia.

Preferably, the hydrogel and/or the oleogel of the invention is(are) administered by injection for example by sub-cutaneous injection, by intramuscular injection or by intra-tumoral injection, preferably by sub-cutaneous injection or by intra-tumoral injection.

The invention also relates to the use of a hydrogel and/or an oleogel such as defined above for the manufacture of a medicament for the prevention and/or treatment of vascular diseases or cancers as defined above.

The invention also relates to a method of prevention and/or treatment of a disease selected from the group consists of vascular diseases and cancers, said method comprising the administration of a pharmaceutical acceptable amount of a hydrogel and/or an oleogel as defined above to a patient in need thereof.

In the context of the invention, the term "treating" or "treatment", as used herein, means reversing, alleviating, inhibiting the progress of the disorder or condition to which such term applies, or one or more symptoms of such disorder or condition.

The hydrogel and/or oleogel according to the invention may further comprise one or more pharmaceutically acceptable carriers. As used herein, the term "pharmaceutically acceptable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art and need not be limited based on formulation.

The hydrogel and/or oleogel according to the invention can be administered by topical or systemic administration, including oral, rectal, nasal, buccal, ocular, sublingual, transdermal, rectal, topical, vaginal, parenteral (including subcutaneous, intra-arterial, intramuscular, intravenous, intradermal, intrathecal and epidural), intracisternal and intraperitoneal. It will be appreciated that the preferred route may vary with for example the condition of the recipient.

The formulations can be prepared in unit dosage form by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

EXAMPLES

Materials Used in the Examples

Figure 1:
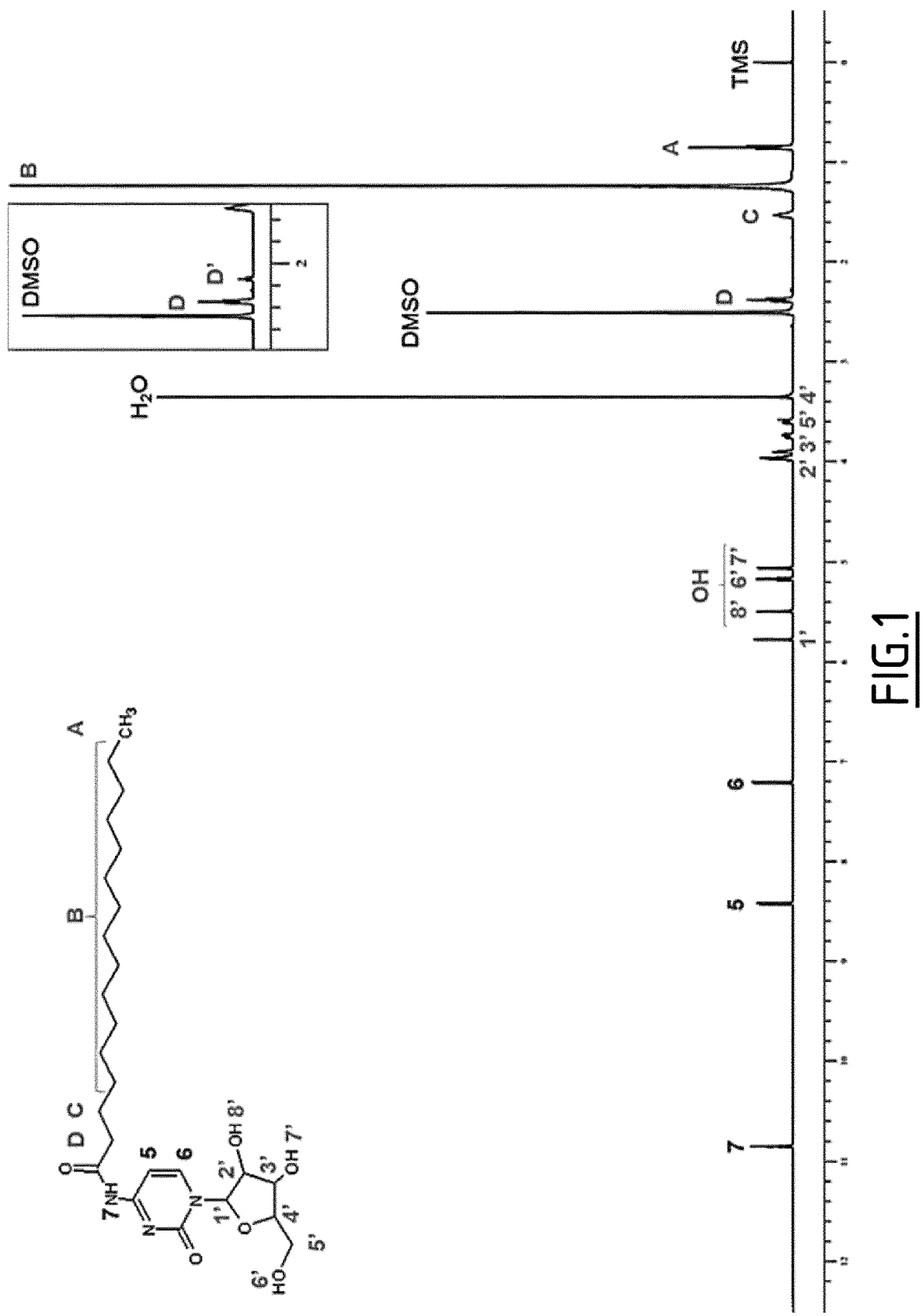
FIG. 1: 1H NMR spectrum of Ia 4-(N)-palmitoyl cytidine et attributions (Insert: 1H NMR spectrum of non-purified 4-(N)-palmitoyl cytidine).

| Suppliers | Compounds |
| --- | --- |
| Gattefossé S.A. (Saint-Priest, France) | Labrafac ® WL 1349 (Labrafac) (caprylic - capric acid triglycerides) |
| BASF (Ludwigshafen, Germany) | Kolliphor ® HS15 (Kolliphor) (mixture of free polyethylene glycol 660 and polyethylene glycol 660 hydroxystearate) |
| Milli-Q plus system (Millipore, Paris, France) | Deionised Water |
| Sigma - Aldrich (St Quentin-Fallavier, France) | Span ® 80 (Span 80) (Sorbitane monooleate) |
| | Dodecanoïc anhydride |
| | Myristic anhydride |
| | Oleic anhydride |
| | Stearic anhydride |
| | Palmitic anhydride |
| | Sodium chloride (NaCl) |
| | Urea |
| | Nile red (9-diethylamino-5H-benzo[α]phenoxazine-5-one) |
| | Cytidine (Cyt) |
| | DMSO (Dimethyl sulfoxide deuterated) |
| | Silica gel (high-purity grade (Davisil Grade 633), pore size 60 Å, 200-425 mesh particle size) |
| Fisher Scientific (Loughborough, United Kingdom) | Ethanol |
| | Dichloromethane |
| | Methanol |
| | Acetone |
| | Formic acid |
| Life Technologies ® - Thermo Fisher Scientific (Saint Aubin, France) | DiO (3,3'-dioctadécyloxacarbocyanine perchlorate) |

Example 1: Synthesis of Modified Cytidine c) Method:

Anhydride of fatty-acid was dissolved in dioxane at final concentration of 50 mg·mL$^{-1}$. This solution was heated to 50° C. on a water bath. An aqueous solution of cytidine (50 mg·mL$^{-1}$) was then added drop by drop. The mixture was mixed under magnetic stirring at 50° C. for one night. The reaction was monitored by thin-layer chromatography (Silica gel on TLC Alu foils, Sigma-Aldrich, St Quentin-Fallavier, France). The components were eluted by dichloromethane/methanol 85/15 (v/v) and observed under UV light (UV-Light, VL-6.C, 6 W 254 nm; Fisher Bioblock Scientific, Illkirch, France). Evaporation under vacuum was performed at 35° C. to remove reaction solvents. The residue was purified by silica gel column flash chromatography (elution with a mixture of dichloromethane/ethanol between 100/0 and 85/15 v/v). Pure fractions were gathered and evaporated under vacuum to obtain a white product, modified cytidine, as the main product. The purity of the compound was controlled by 1H NMR on an Avance DRX 500 MHz (Bruker Daltonics GmbH, Bremen, Germany) in deuterated dimethylsulfoxide.

d) Results:

Different anhydride of fatty acids: Lauric anhydride (C12), Myristic anhydride (C14), Palmitic anhydride (C16), Oleic anhydride (C18:1) and Stearic anhydride (C18), were tested to modify the cytidine molecule via amide bond formation, and the 5 different molecules were obtained: 4-(N)-lauroyl cytidine (Cyt-C12), 4-(N)-myristoyl cytidine (Cyt-C14), 4-(N)-palmitoyl cytidine (Cyt-C16), 4-(N)-oleoyl cytidine (Cyt-C18:1) and 4-(N)-stearoyl cytidine (Cyt-C18), with different synthesis yield (Table 1).

TABLE 1

Molecular formula, molecular weight and synthesis yield.

| Molecule | Molecular formula | Molecular weight (g · mol$^{-1}$) | Molar synthesis yield (%) |
|---|---|---|---|
| Cyt-C12 | $C_{21}H_{35}N_3O_6$ | 425.5 | 35-40 |
| Cyt-C14 | $C_{23}H_{39}N_3O_6$ | 453.6 | 35-40 |
| Cyt-C16 | $C_{25}H_{43}N_3O_6$ | 481.6 | 30-35 |
| Cyt-C18:1 | $C_{27}H_{45}N_3O_6$ | 507.7 | 5-10 |
| Cyt-C18 | $C_{27}H_{47}N_3O_6$ | 509.7 | 25-30 |

Figure 2:
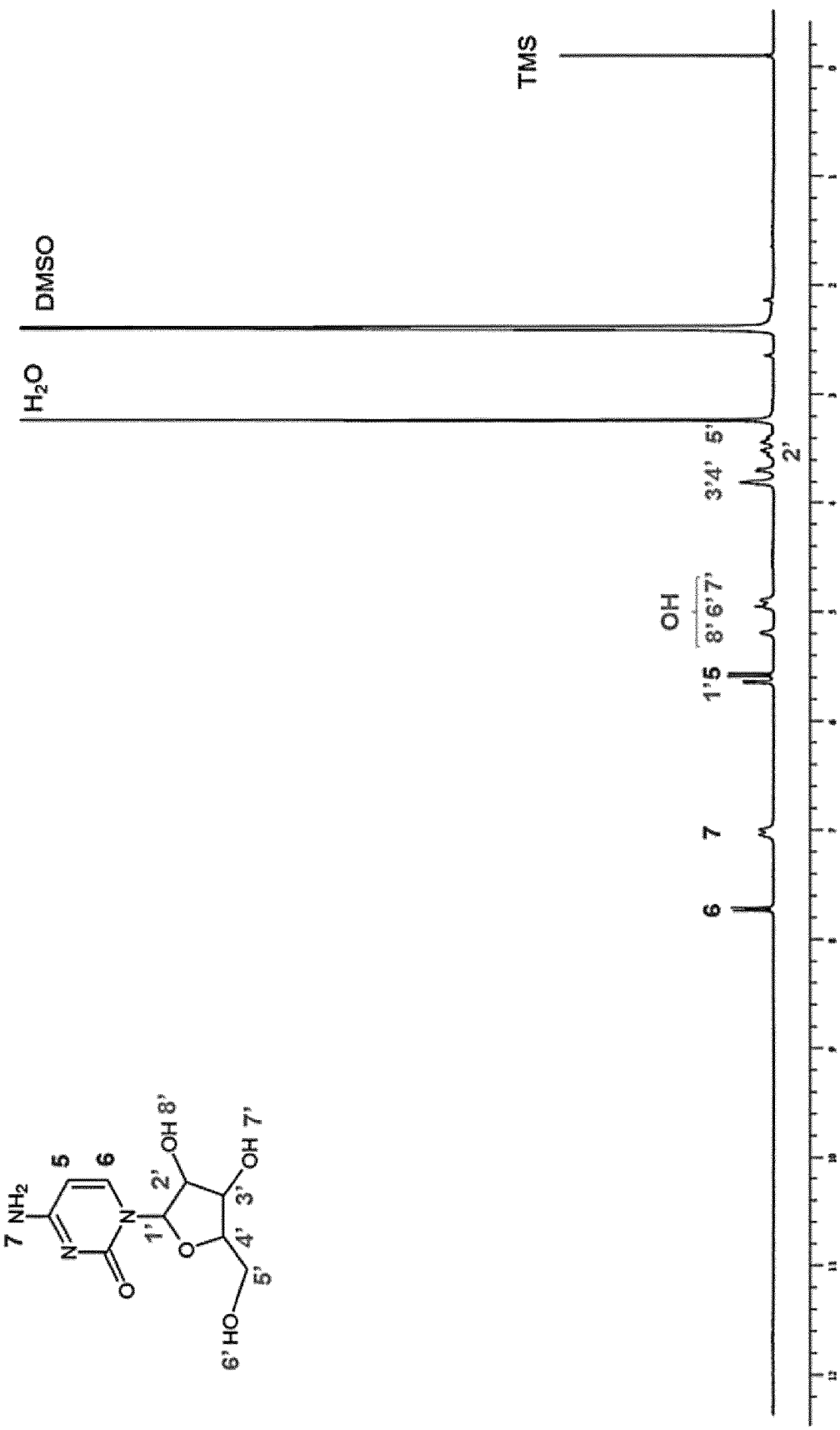
FIG. 2: 1H NMR spectrum of cytidine.

All molecules were characterized by 1H NMR, and compared to non-modified cytidine (see FIGS. 1 and 2). The purity of the molecules was confirmed by peak integration and the presence of only one peak between 2 and 2.2 ppm ($CH_2$ in alpha position from the amide bond). The presence of 2 peaks is characteristic of the presence of $CH_2$ in alpha position from the amide bond (synthesized molecule) and $CH_2$ in alpha position from the ester bond (excess of anhydride derivatives).

1H NMR Characterization of 4-(N)-Palmitoyl Cytidine (Cyt-C16):

1H NMR ((CD3)2SO, ppm): 10.85 (1H, s, NHCO), 8.43 (1H, d, 5-CH), 7.20 (1H, d, 6-CH), 5.77 (1H, m, 1'-CH), 5.50 (1H, d, 8'-OH), 5.18 (1H, t, 6'-OH), 5.07 (1H, d, 7'-OH) 3.96 (1H, m, 2'-CH), 3.90 (1H, m, 3'-CH), 3.76-3.72 (2H, m, 5'-CH), 3.61-3.57 (1H, m, 4'-CH), 2.36 (2H, t, CO—CH2), 1.53 (2H, t, CO—CH2-CH2), 1.23 (24H, m, CH2(CH2) 12CH3), 0.85 (3H, t, CH3).

NMR $^1$H Characterization of Cytidine:

1H-NMR ((CD3)2SO, ppm): 7.84 (1H, d, 6-CH), 7.14 (2H, d, NH2), 5.74 (1H, d, 1'-CH), 5.67 (1H, d, 5-CH), 5.29 (1H, d, 8'-OH), 5.05 (1H, t, 6'-OH), 4.99 (1H, d, 7'-OH), 3.91 (2H, m, 3'-CH et 4'-CH),), 3.85 (1H, m, 2'-CH), 3.61-3.54 (1H, m, 5'-CH).

Example 2: Cyt-C16-Loaded Lipid Nanocapsules and Hydrogels Formation c) Method:

The LNCs formulation was based on a phase-inversion process, from oil-in-water emulsion at low temperature to water-in-oil emulsion at high temperature. The quantities of oil phase (Labrafac), aqueous phase (water and NaCl) and surfactants (Kolliphor and Span 80) for each formulation were precisely weighed. For 25 nm-diameter LNCs, $m_{Labrafac}$=0.6 g, $m_{Kol}$=1.8 g, $m_{Span80}$=0.3 g, $m_{Water}$=1.3 g and $m_{NaCl}$=0.054 g; for 50 nm-diameter LNCs, $m_{Labrafac}$=1.1168 g, $m_{Kol}$=0.9168 g, $m_{Span80}$=0.45 g, $m_{Water}$=1.5168 g and $m_{NaCl}$=0.054 g; for 75 nm-diameter LNCs, $m_{Labrafac}$=1.8 g, $m_{Kol}$=1.3 g, $m_{Span80}$=0.3 g, $m_{Water}$=0.6 g and $m_{NaCl}$=0.054 g; for 100 nm-diameter LNCs, $m_{Labrafac}$=1.8 g, $m_{Kol}$=0.95 g, $m_{Span80}$=0.3 g, $m_{Water}$=0.95 g and $m_{NaCl}$=0.054 g.

4-(N)-palmitoyl cytidine (Cyt-C16) was firstly solubilised in a mixture of Labrafac, Span 80 and acetone, at concentrations from 1 to 5% (w/w$_{Labrafac}$) at 60° C., and acetone was evaporated. Then, Kolliphor and the aqueous phase were added and the mixture was heated to 75° C. under magnetic stirring followed by cooling to 45° C. (rate of 5° C.·min$^{-1}$). This cycle was repeated three times and during the last temperature decrease at the phase-inversion temperature (about 60° C.), an irreversible shock was induced by dilution with 2 mL of pure water. Afterwards, slow magnetic stirring was applied to the suspension of LNCs at room temperature, and a hydrogel was spontaneously formed. The gelation process was completed after 24 h at 4° C. Prior completed gelation, a part of the formulation was diluted by a factor of 60 (v/v) with pure water. The hydrodynamic diameter (Z-Average), polydispersity index (PdI), and zeta potential (Pz) were measured to confirm the presence of LNCs in the diluted suspensions.

Z-ave, PdI, and Pz of LNCs were determined by dynamic light scattering on a Zetasizer® Nano ZS (Malvern Instruments S.A., Worcestershire, United Kingdom). The helium neon laser, 4 mW, was operated at 633 nm, with the scattering angle fixed at 173° and the temperature at 25° C. The curve fittings of the correlation functions were performed using an exponential fit (Cumulant approach) for Z-Ave and PdI determinations for the LNCs suspensions. Smoluchowski's approximation was used to determine the electrophoretic mobility for Pz determination.

The Cyt-C16 concentrations in the hydrogels of LNCs were determined using a LC-MS/MS apparatus: Alliance® 295 system (Waters, Saint-Quentin-en-Yvelines, France) with a Zorbax—Eclipse XDB-C18 column 4.6×150 mm, 3.5 µm, (Agilent Technologies, Santa Clara, United States). The temperature was fixed to 25° C. The mobile phase consisted of methanol with formic acid 0.1% (v/v), at a flow rate of 0.8 mL·min$^{-1}$. The injection volume was 10 µL. The total HPLC effluent was directed into a Quattro Micro® triple quadrupole mass spectrometer (Waters Saint-Quentin-en-Yvelines, France). Ionization was achieved using turbo ion spray in positive ion mode. The mass spectrometer operated in multiple reactions monitoring (MRM) mode. The (M–H)+ m/z transitions for Cyt-C16 was 482>112 and 482>350. Cyt-C16 was diluted in methanol at concentration from 1.25 to 200 ng·mL$^{-1}$, in presence of non-loaded LNCs, for the calibration curve. A volume of 50 µL of hydrogels was dissolved with deionized water at 1:4000 (v/v), to obtain a complete dispersion of LNCs. Then, a volume of 100 µL was mixed with 900 µL of methanol. Quantification of Cyt-C16 was achieved after filtration of this solution on 0.22-µm filter.

d) Results:

The phase-inversion process allows the formulation of LNCs in suspension, with a monomodal and monodisperse distribution and Pz values close to neutrality (Table 2). When Cyt-C16 was added to the formulation process, the LNCs suspension turned into a hydrogel. Gels can be dissolved in an excess of water and LNCs were still visible, showing the physical character of the gel association.

The presence of Cyt-C16 did not modify the physico-chemical properties of LNCs formulation (Table 2). The data were representative of a monomodal and a monodisperse size distribution, with values close to those obtained for non-loaded LNCs. Only the diameters of the LNCs were slightly decreased.

sample. Oscillatory strain sweeps at 1 Hz constant frequency were performed to determine the linear regime characterized by constant dynamic moduli (elastic: G' and viscous: G" moduli), independent of the strain amplitude. In this regime (0.1% constant shear strain), G' and G' were measured as a function of angular frequency (0.1 to 10 Hz). In addition, a temperature ramp from 25 to 70° C. (2° C.·min$^{-1}$) was performed at 0.01% constant shear strain and 1 Hz constant angular frequency. The viscoelastic properties of hydrogels were studied, with LNC diameter from 25 to 100 nm, with Cyt-C16 1 and 2.5% (w/w$_{Labrafac}$) and with LNC concentration from 12.5 to 410 mg·mL$^{-1}$. All these experiments were repeated in triplicate.

d) Results:

Oscillatory strain sweeps at 1 Hz constant frequency were performed to determine the linear regime, characterized by constant dynamic moduli (elastic G' and viscous G" moduli), independent of the strain amplitude. The limit of the linear regime corresponded to a shear strain of 0.6% (data not

TABLE 2

Size distribution (Z-average and PdI) and zeta potential of non-loaded LNCs or LNCs loaded with Cyt-C16 2.5% (w/w$_{Labrafac}$) (mean ± SD).

|  | Cyt-C16 2.5% (w/w$_{Labrafac}$) | | | | Cyt-C16 0% (w/w$_{Labrafac}$) | | | |
| --- | --- | --- | --- | --- | --- | --- | --- | --- |
|  | 25 nm | 50 nm | 75 nm | 100 nm | 25 nm | 50 nm | 75 nm | 100 nm |
| Z-average (nm) | 25 ± <1 | 51 ± 3 | 71 ± 10 | 88 ± 6 | 25 ± <1 | 56 ± 2 | 76 ± 2 | 107 ± 4 |
| PdI | 0.04 ± 0.01 | 0.06 ± 0.04 | 0.06 ± 0.01 | 0.08 ± 0.02 | 0.08 ± 0.04 | 0.06 ± 0.03 | 0.07 ± 0.02 | 0.90 ± 0.02 |
| PZ (mV) | −2 ± 1 | −4 ± 2 | −4 ± 2 | −3 ± 2 | −2 ± 2 | −4 ± 2 | −3 ± 1 | −4 ± 1 |
| n = | 3 | 12 | 3 | 12 | 7 | 7 | 7 | 7 |

For the four hydrogels, 100% of the initial amount of Cyt-C16 added to the formulation was found (Table 3). In addition to confirming that all of Cyt-C16 is recovered, this result indicates that the formulation process does not degrade the molecule. Indeed, a modification of Cyt-C16 (opening of the cycle or break) would have led to a variation in the molar mass of the molecule. The degraded molecules would then no longer have been assayed as Cyt-C16 using LC-MS/MS.

TABLE 3

Cyt-C16 concentration (w/w$_{Labrafac}$) and pourcentage of (n = 3; mean ± SD).

| LNC diameter | Cyt-C16 (w/w$_{Labrafac}$) | % |
| --- | --- | --- |
| 50 nm | 2.5% | 102.04 ± 8.82 |
|  | 1% | 106.57 ± 5.23 |
| 100 nm | 2.5% | 98.64 ± 3.36 |
|  | 1% | 96.02 ± 1.38 |

Example 3: Viscoelastic Properties of the Hydrogels of the Invention c) Method:

The viscoelastic properties of the hydrogels of LNCs at 25° C. were measured using a Kinexus® rheometer (Malvern Instruments S.A., United Kingdom), with a cone plate geometry (diameter 40 mm, angle: 2°). The hydrogels were deposited directly on the plate geometry of the rheometer and the cone geometry was placed in contact with the shown), and all the viscoelastic properties of the hydrogels were determined in the linear regime, at shear strain of 0.1%.

Figure 3:
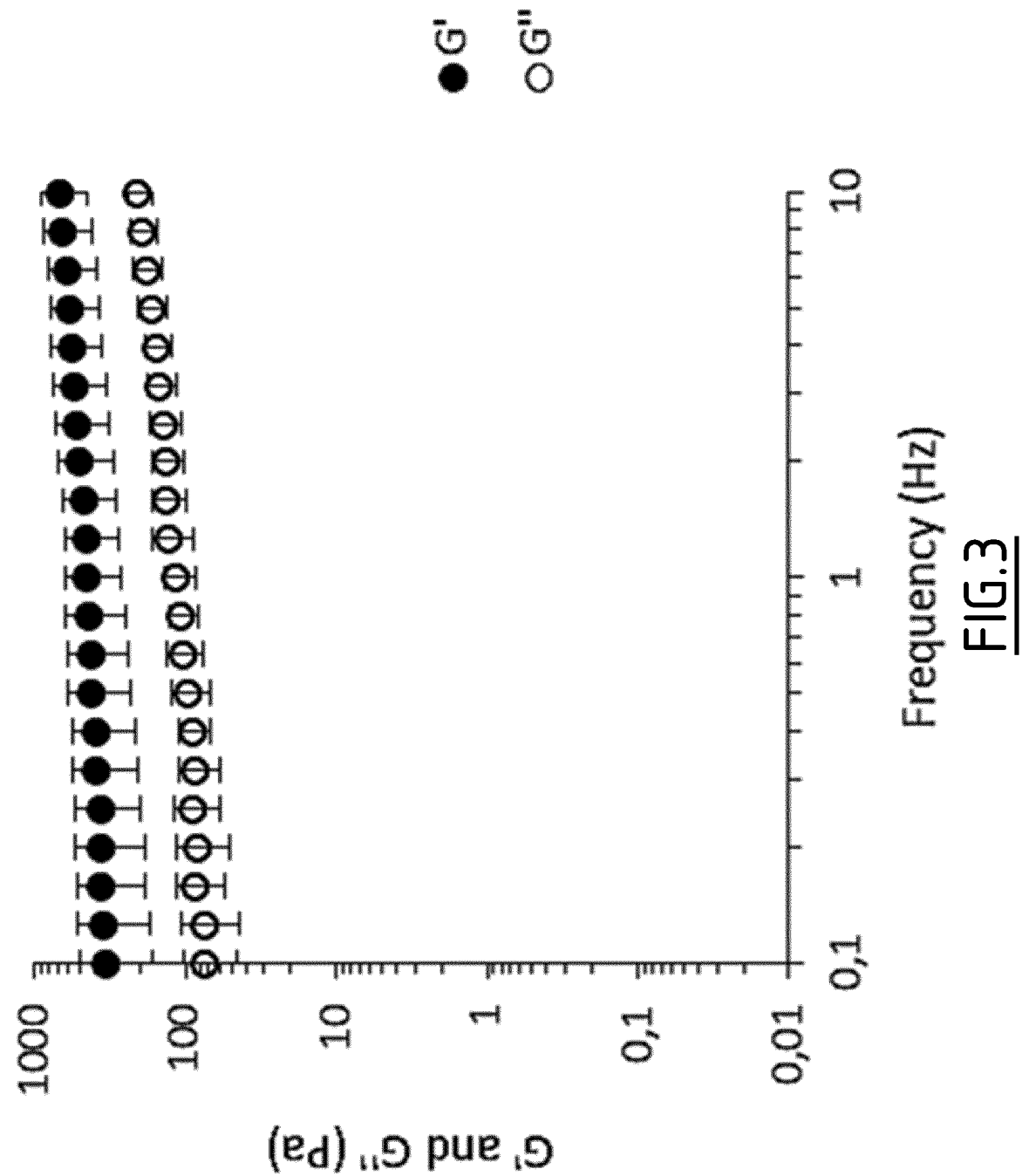
FIG. 3: Elastic G' (●) and viscous G" (○) moduli vs frequency, for a hydrogel with Cyt-C16 2.5% (w/w$_{Labrafac}$), LNC diameter: 50 nm and LNC concentration 410.2 mg·mL$^{-1}$. Constant shear strain: 0.1% (n=3, mean±SD).

For example, the rheogram obtained for the hydrogel of LNCs (LNC diameter: 50 nm, LNC concentration: 410.2 mg·mL$^{-1}$, Cyt-C16 2.5% (w/w$_{Labrafac}$)) is reported in FIG. 3. The rheogram obtained is characteristic of a gel. The values of G' were always higher than those of G": about 300 and 100 Pa at oscillation frequency of 1 Hz, respectively; and remained relatively constant irrespective of the oscillation frequency. The ratio G"/G' were comprised between 0.2 and 0.33, confirming a low value for the phase angle between the shear strain and the shear stress responses (between 11 and 18°). These values show good elastic for the hydrogels.

Figure 4:
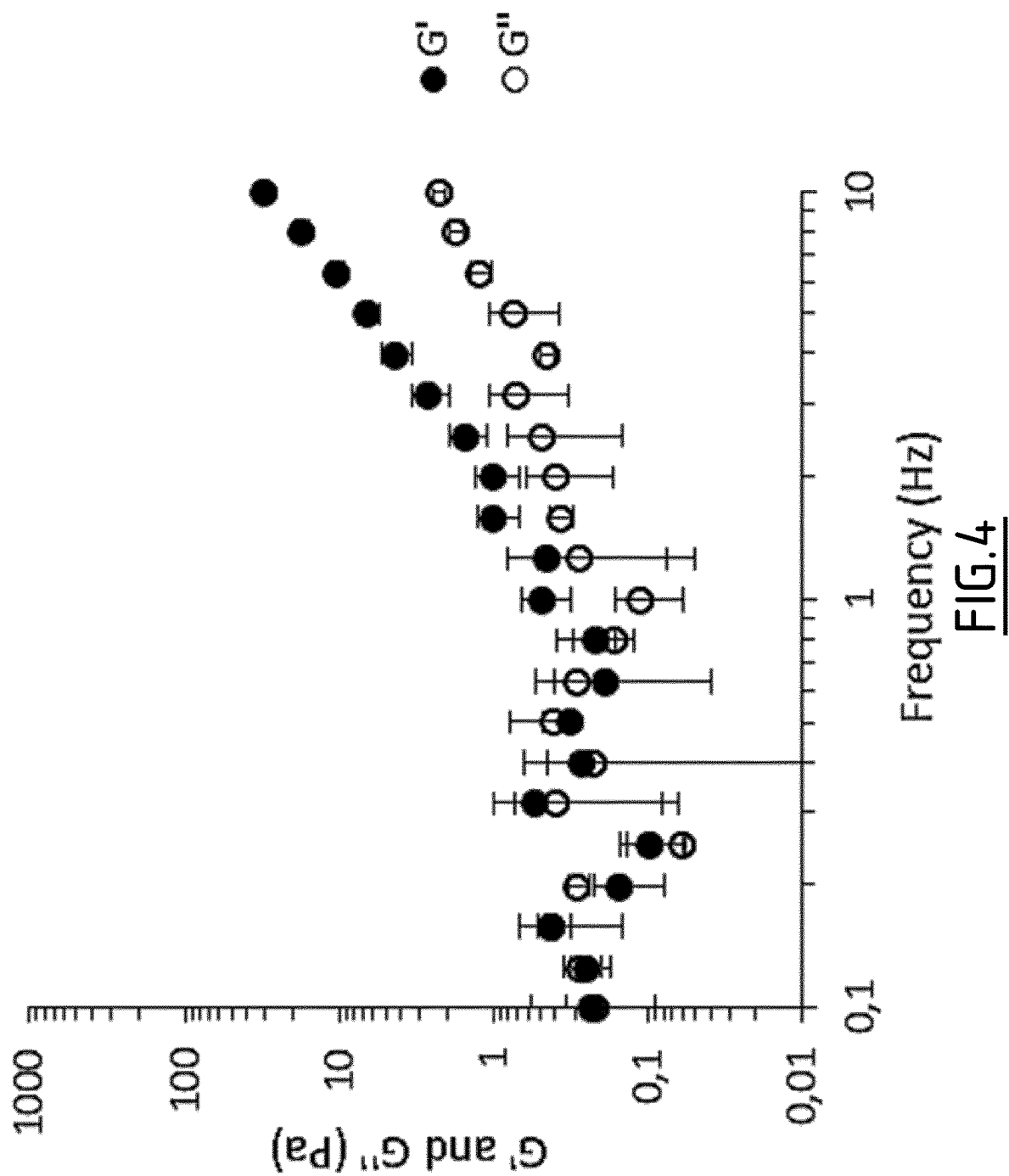
FIG. 4: Elastic G' (●) and viscous G" (○) moduli vs frequency, for a LNC suspension (no Cyt-C16), LNC diameter: 50 nm and LNC concentration 410.2 mg·mL$^{-1}$. Constant shear strain: 0.1% (n=3, mean±SD).

Without Cyt-C16, the phase inversion process led to usual LNCs in suspension. The viscoelastic properties of LNCs (LNC diameter: 50 nm, LNC concentration: 410.2 mg·mL$^{-1}$, Cyt-C16 0% (w/w$_{Labrafac}$)) are reported in FIG. 4. In order to compare the 2 materials (hydrogel and suspension), we studied the viscoelastic properties of the LNC suspension with a constant shear strain of 0.1% even if this parameter was not adjusted to the suspension forms (not reliable shear stress response, below the detection limit of the rheometer). The variation profiles of G' and G" were too noisy, with low modulus values (between 0.1 and 1 Pa at oscillation frequency of 1 Hz).

Figure 5:
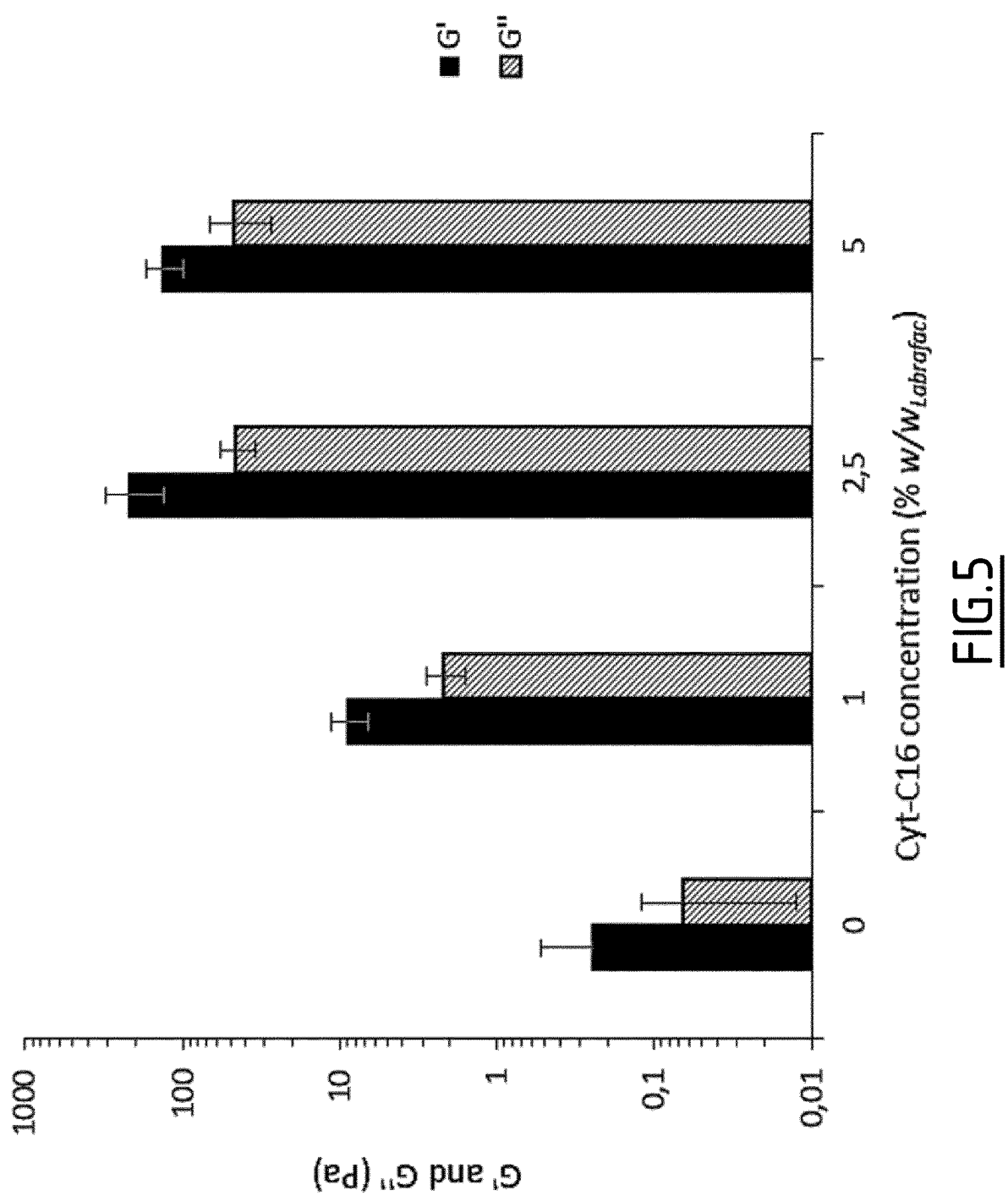
FIG. 5: Elastic G' (black bar) and viscous G" (hatched bar) moduli vs Cyt-C16 concentration, for the hydrogels, with LNC diameter: 50 nm and LNC concentration: 300 mg·mL$^{-1}$. Ocillation frequency: 1 Hz and shear strain: 0.1% (n=3, mean±SD).

The influence of the Cyt-C16 concentration was reported in FIG. 5, for hydrogels of LNCs (LNC diameter: 50 nm and LNC concentration: 300 mg·mL$^{-1}$). The viscoelastic properties of the hydrogels of LNCs were directly related to the Cyt-C16 concentration, used during the formulation process. Higher the concentration of Cyt-C16, and more important the values of the G' and G" moduli. The hydrogels obtained with Cyt-C16 2.5% (w/w$_{Labrafac}$) makes it possible to obtain values of G' and G" moduli 20-fold higher than those obtained with Cyt-C16 1% (w/w$_{Labrafac}$). In addition, the ratios G"/G' were always comprised between 0.2 and 0.33 (corresponding to phase angle comprised between 11 and 18°), irrespective of the concentration of Cyt-C16. It proved that the elastic properties of the hydrogels were preserved.

Figure 6:
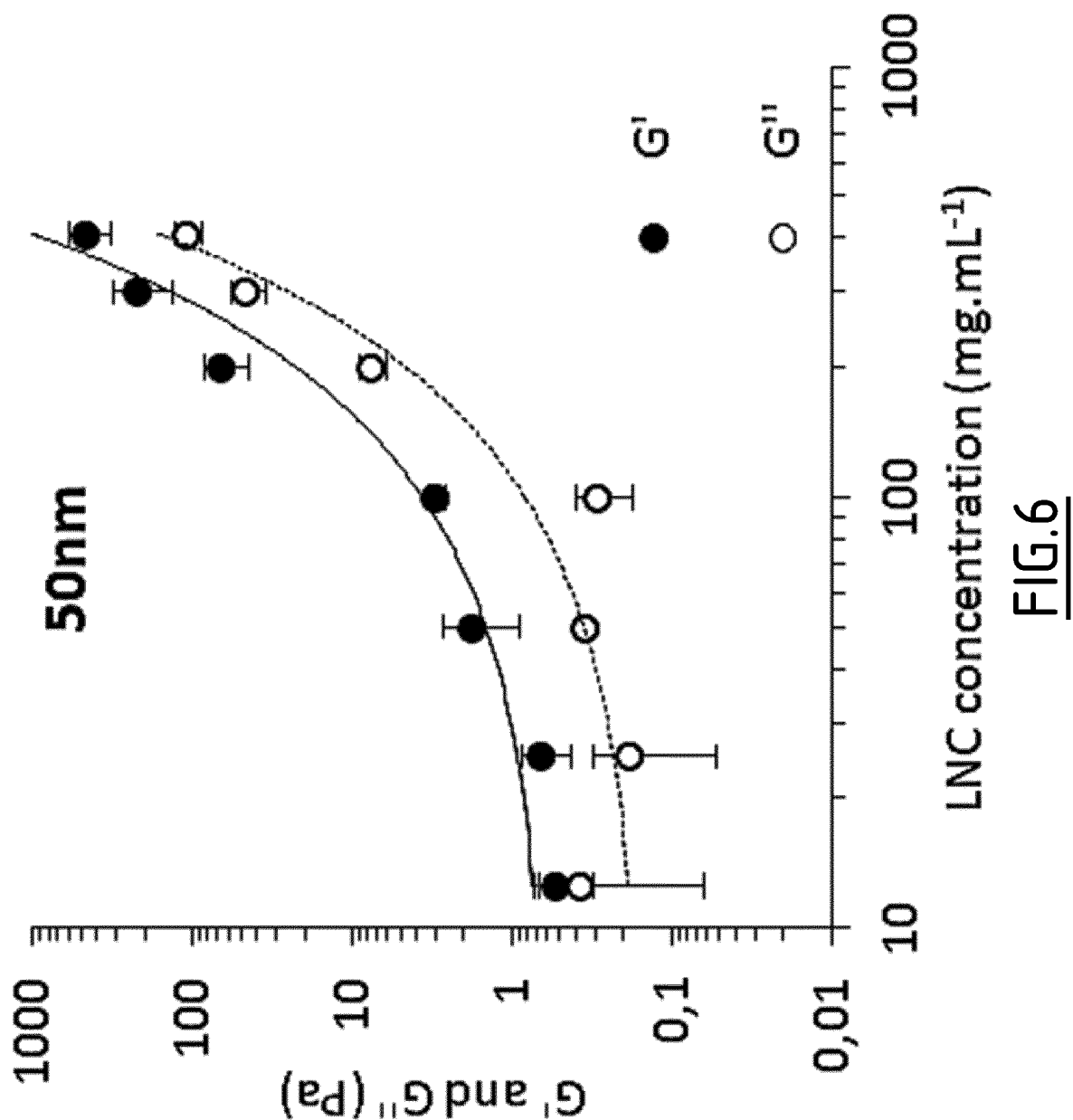
FIGS. 6 to 8: Elastic G' (full symbol) and viscous G" (empty symbol) moduli vs LNC concentration, for the hydrogels, with Cyt-C16 2.5% (w/w$_{Labrafac}$). Ocillation frequency: 1 Hz and shear strain: 0.1%. LNCs diameter: 50 (●○), 75 (▲△) and 100 nm (♦◇) (n=3, mean±SD).
Figure 7:
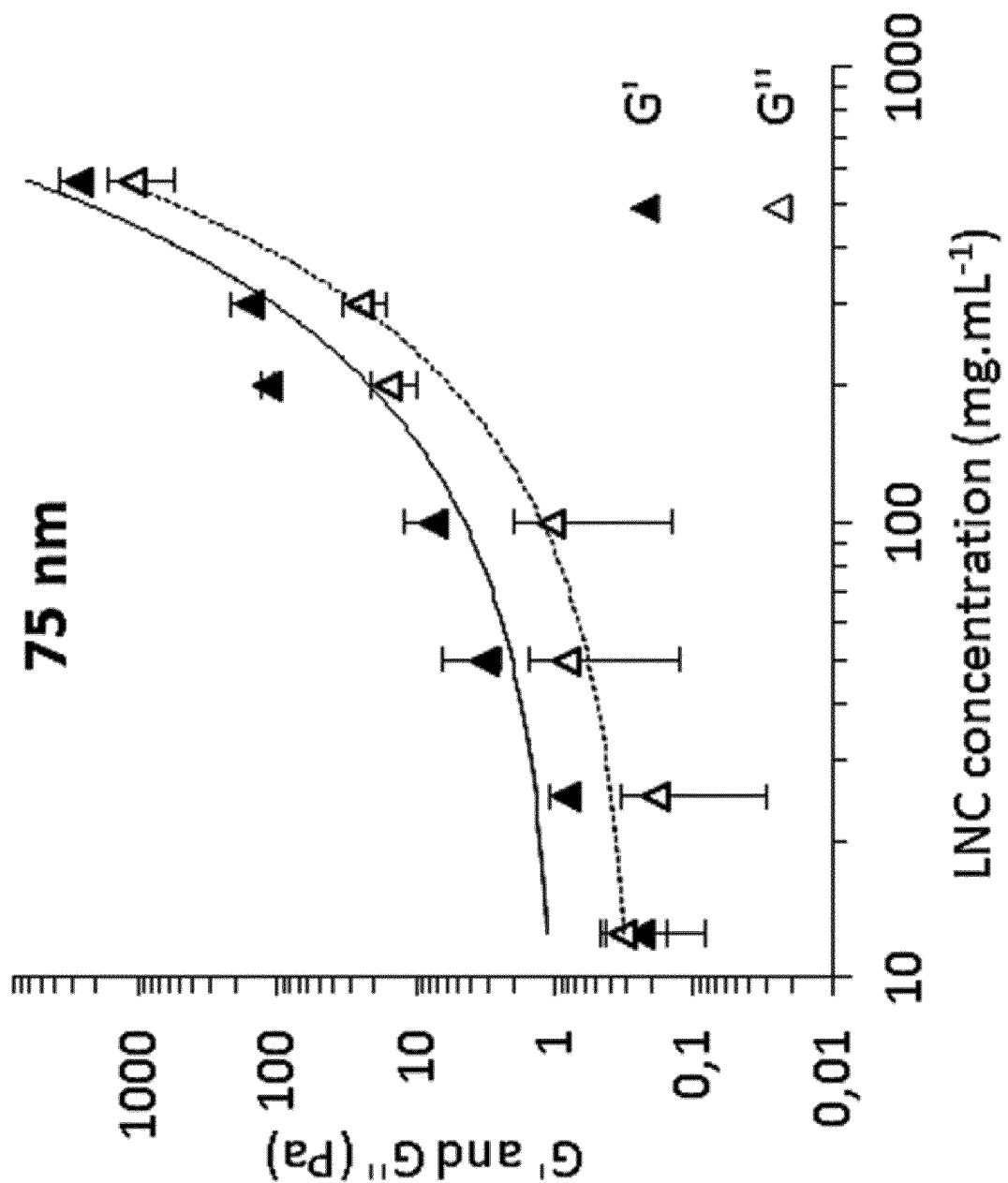
Figure 8:
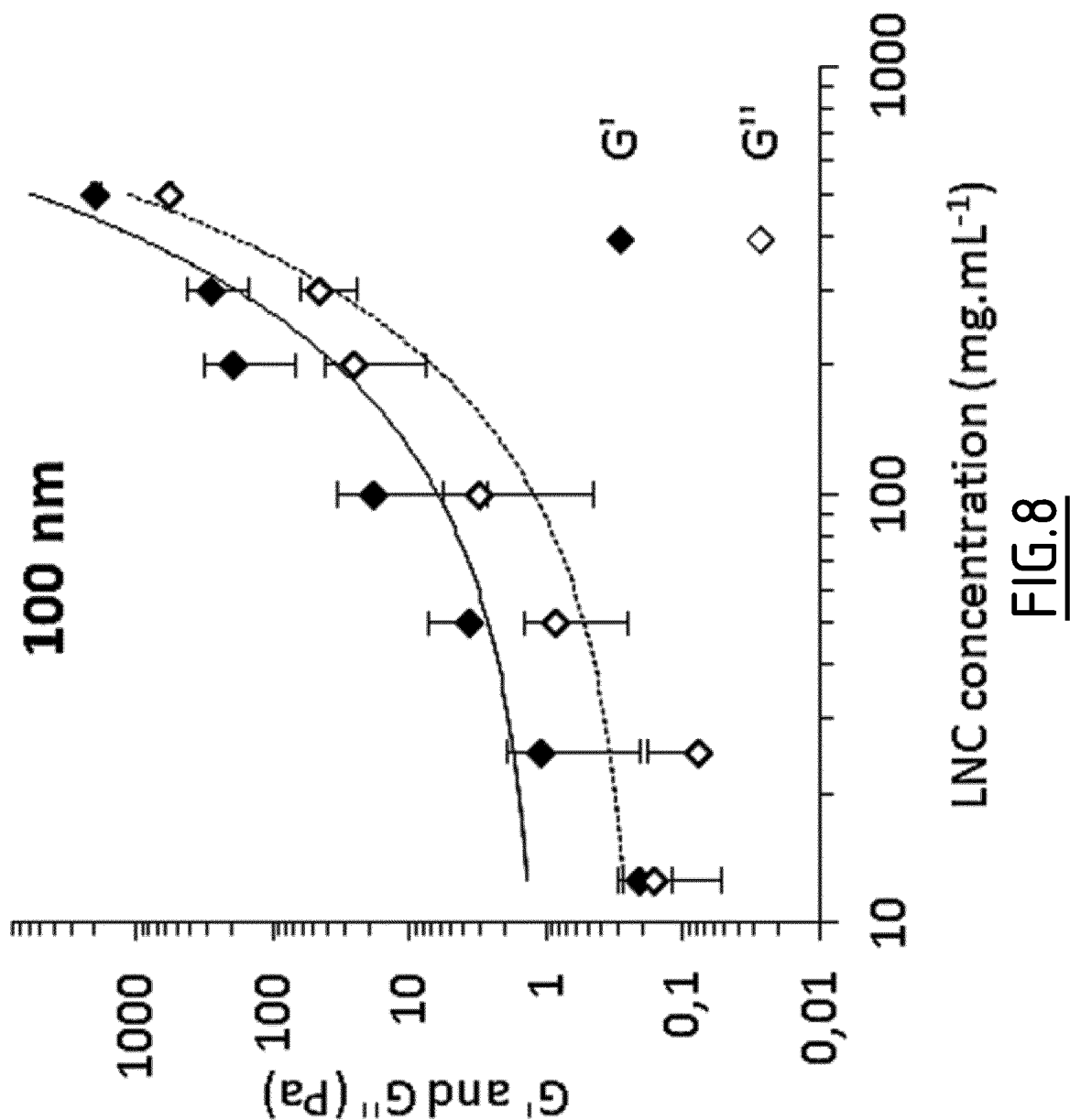

The influence of the LNC concentration was reported in FIGS. 6 to 8, for hydrogels of LNCs (LNC diameter: 50, 75 and 100 nm and Cyt-C16 2.5% (w/w$_{Labrafac}$)). At the maximum concentrations of LNCs in the study, "rigid" hydrogels with similar properties were obtained. When the hydrogels are diluted, they gradually became fluid, with a decrease of the values of G' and G" moduli. Below a LNC concentration of 50 mg·mL$^{-1}$, the values of G' and G" reached those of NCLs without Cyt-C16. The characterization of the viscoelastic properties of hydrogel dilutions containing Cyt-C16 1% (w/w$_{Labrafac}$) (LNC diameters of 50, 75 and 100 nm) was also carried out (data not shown). The same behavior was observed: a continuous decrease of the values of G' and G" moduli with the continuous dilution of the hydrogels. The LNCs in suspension were obtained for LNC concentrations at 200 mg·mL$^{-1}$.

Finally, the influence of temperature on the viscoelastic properties of hydrogels has been studied. A solid-liquid phase transition temperature was determined, corresponding to the transition from the hydrogel state to a viscous state. The results obtained are presented in Table 4. The size of the LNCs had an influence on the phase transition temperature. Indeed, for the LNCs with diameters 75 and 100 nm, the transition temperatures were higher than 70° C. Whereas for 50-nm diameter LNCs, the transition temperatures are 38 and 51° C., for Cyt-C16 concentrations of 1 and 2.5% (w/w$_{Labrafac}$), respectively.

TABLE 4

Solid-to-Liquid transition temperature of the hydrogels (n = 3, mean ± SD).

|  | LNC 50 nm | LNC 75 nm | LNC 100 nm |
| --- | --- | --- | --- |
| LNC concentration (mg · mL$^{-1}$) | 410.2 | 516.6 | 503.8 |
| Cyt-C16 1% (w/w$_{Labrafac}$) | 38° C. ± 6 | >70° C. | >70° C. |
| Cyt-C16 2.5% (w/w$_{Labrafac}$) | 51° C. ± 6 | >70° C. | >70° C. |

Example 4: Cyt-C16 Based Oleogel c) Method:

Cyt-C16 was solubilized in Labrafac at 70° C. under magnetic stirring. Then, after coiling at 4° C., a gel, called oleogel, was spontaneously obtained. The viscoelastic properties of the oleogels (Cyt-016 from 0.005 to 0.2 mmol·g$^{-1}$ of Labrafac, corresponding to Cyt-C16 from 0.25 to 9.95% (w/w$_{Labrafac}$)), at 25° C. were measured using a Kinexus® rheometer (Malvern Instruments S.A., United Kingdom), with a plate plate geometry (diameter 20 mm, gap: 800 μm). The oleogels were deposited directly on the bottom plate geometry of the rheometer and the top plate geometry was placed in contact with the sample. Oscillatory strain sweeps at 1 Hz constant frequency were performed to determine the linear regime characterized by constant dynamic moduli (elastic: G' and viscous: G" moduli), independent of the strain amplitude. In this regime (0.01% constant shear strain), G' and G' were measured as a function of angular frequency (0.1 to 10 Hz). In addition, a temperature ramp from 25 to 70° C. (2° C.·min$^{-1}$) was performed at 0.01% constant shear strain and 1 Hz constant angular frequency. All these experiments were repeated in triplicate.

d) Results:

Cyt-C16 solubilized in Labrafac at high temperature (70° C.) led to the oil gelation after cooling. Oscillatory strain sweeps at 1 Hz constant frequency were performed to determine the linear regime, characterized by constant dynamic moduli (elastic G' and viscous G" moduli), independent of the strain amplitude. The limit of the linear regime corresponded to a shear strain of 0.05% (data not shown), and all the viscoelastic properties of the oleogels were determined in the linear regime, at shear strain of 0.1%.

Figure 9:
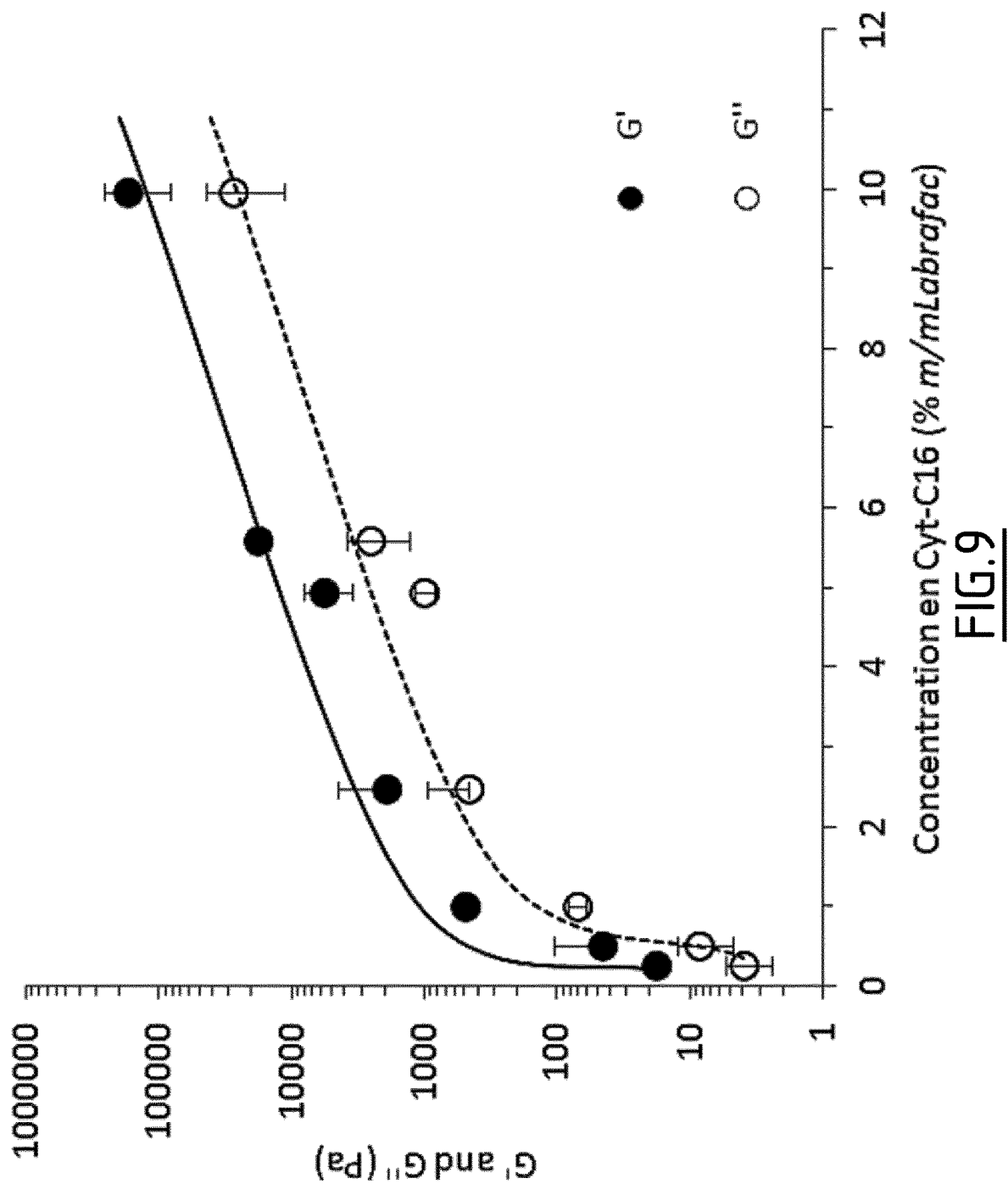
FIG. 9: Elastic G' (●) and viscous G" (○) moduli vs Cyt-C16 concentration, for oleogels. Ocillation frequency: 1 Hz and Shear strain: 0.01% (n=3, mean±SD).

The variation of the values of the elastic G' and viscous G" moduli (at an oscillation frequency of 1 Hz) as a function of the concentration of Cyt-C16 (w/w$_{Labrafac}$) is reported in FIG. 9.

The viscoelastic properties of the oleogels depended on the Cyt-C16 concentration, with high values of G' and G" moduli when Cyt-C16 concentration increased. In addition, for Cyt-C16 concentrations higher than 1% (w/w$_{Labrafac}$), the solid-liquid transition temperature was always higher than 70° C. (data not shown).

Example 5: Stability of LNCs Hydrogels c) Method:

Hydrogels of LNCs with diameters of 50 and 100 nm, loaded with Cyt-C16 2.5% (w/w$_{Labrafac}$), were formulated and put in 5-mL plastic syringe (SOFT-JECT®, HSW, Tuttlingen, Germany) prior completed gelation. The syringes were stored at 4° C. to allow completed gelation. The viscoelastic properties of the hydrogels of LNCs at 25° C. were measured using a Kinexus® rheometer (Malvern Instruments S.A., United Kingdom), with a cone plate geometry (diameter 40 mm, angle: 2°). The hydrogels were deposited directly (without needle) on the plate geometry of the rheometer and the cone geometry was placed in contact with the sample. Oscillatory strain sweeps at 1 Hz constant frequency were performed to determine the linear regime characterized by constant dynamic moduli (elastic: G' and viscous G" moduli), independent of the strain amplitude. In this regime (0.1% constant strain), G' and G' were measured as a function of angular frequency (0.1 to 10 Hz). All these experiments were repeated in triplicate.

Figure 10:
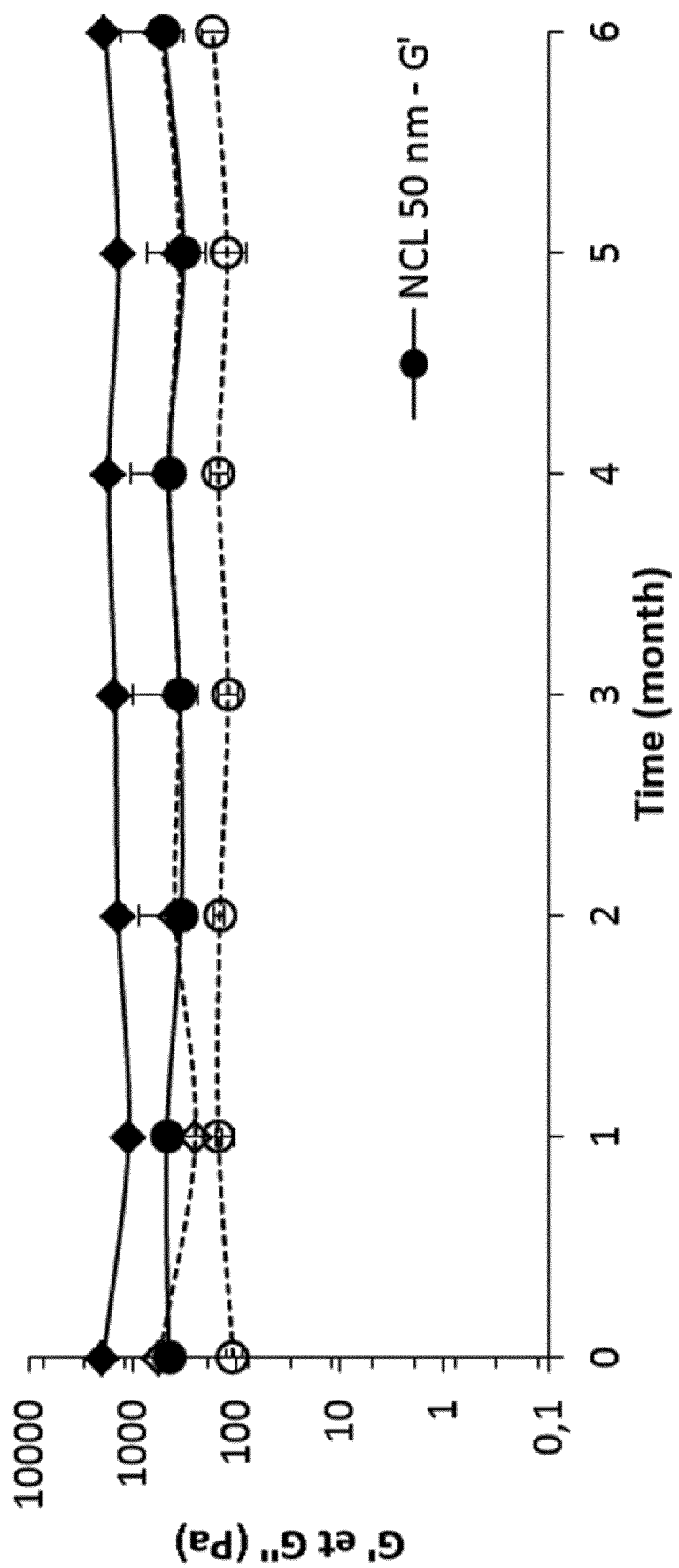
FIG. 10: Elastic G' (full symbol, solid line) and viscous G" (empty symbol, dotted line) moduli for the hydrogels vs time (storage at 4° C.). Oscillation frequency: 1 Hz and shear strain: 0.1%. LNC diameter (nm)/LNC concentration (mg·mL$^{-1}$) for the hydrogels: 50/410.2 (●○) and 100/503.8 (♦◇), loaded with Cyt-C16 2.5% (w/w$_{Labrafac}$) (n=3, mean±SD).
Figure 11:
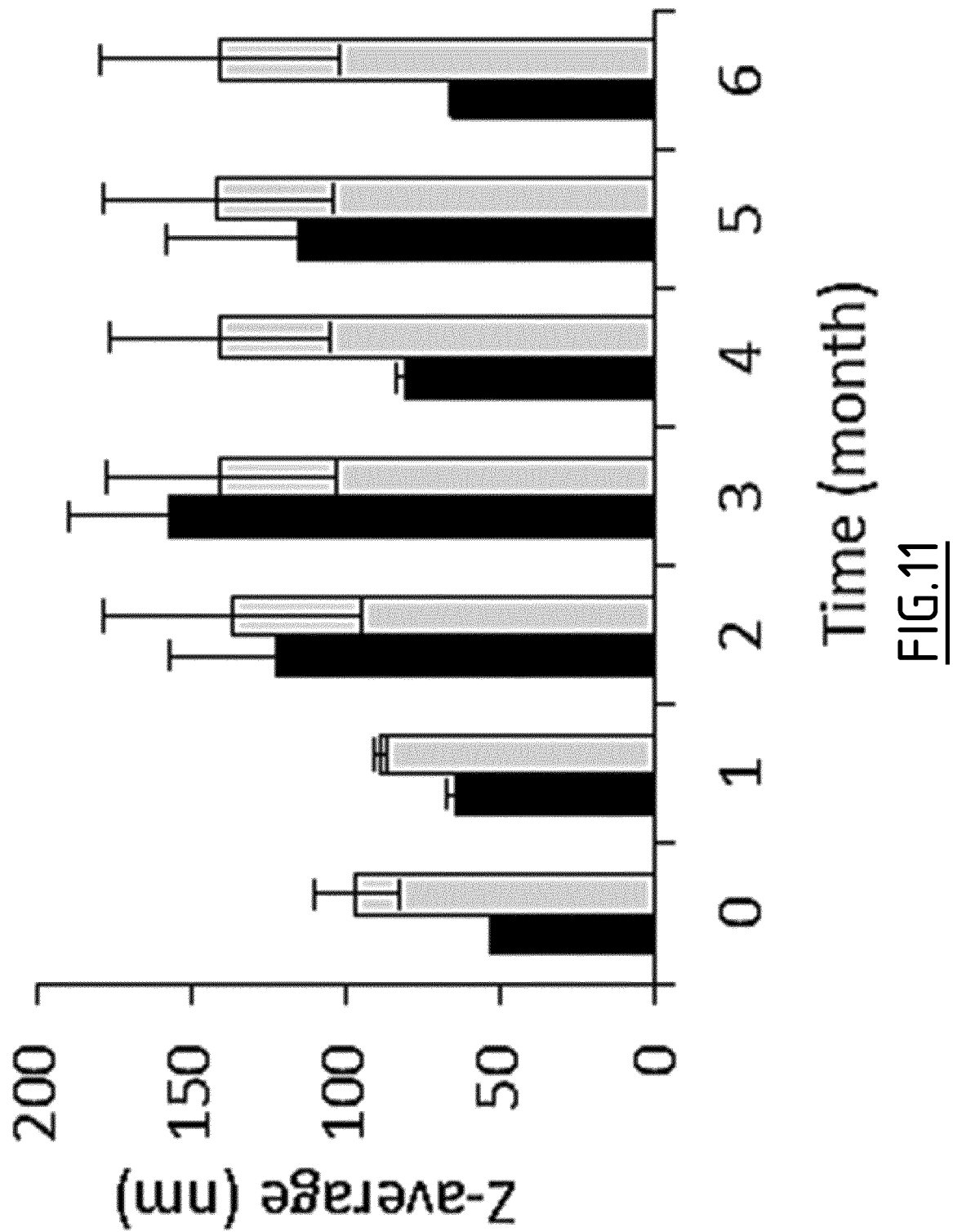
FIGS. 11 and 12: Z-average and PdI of LNCs vs time after the dissolution of the hydrogels, stored at 4° C. LNC diameter (nm)/LNC concentration (mg·mL$^{-1}$) for the hydrogels: 50/410.2 (black bar) and 100/503.8 (grey bar), loaded with Cyt-C16 2.5% (w/w$_{Labrafac}$) (n=3, mean±SD).
Figure 12:
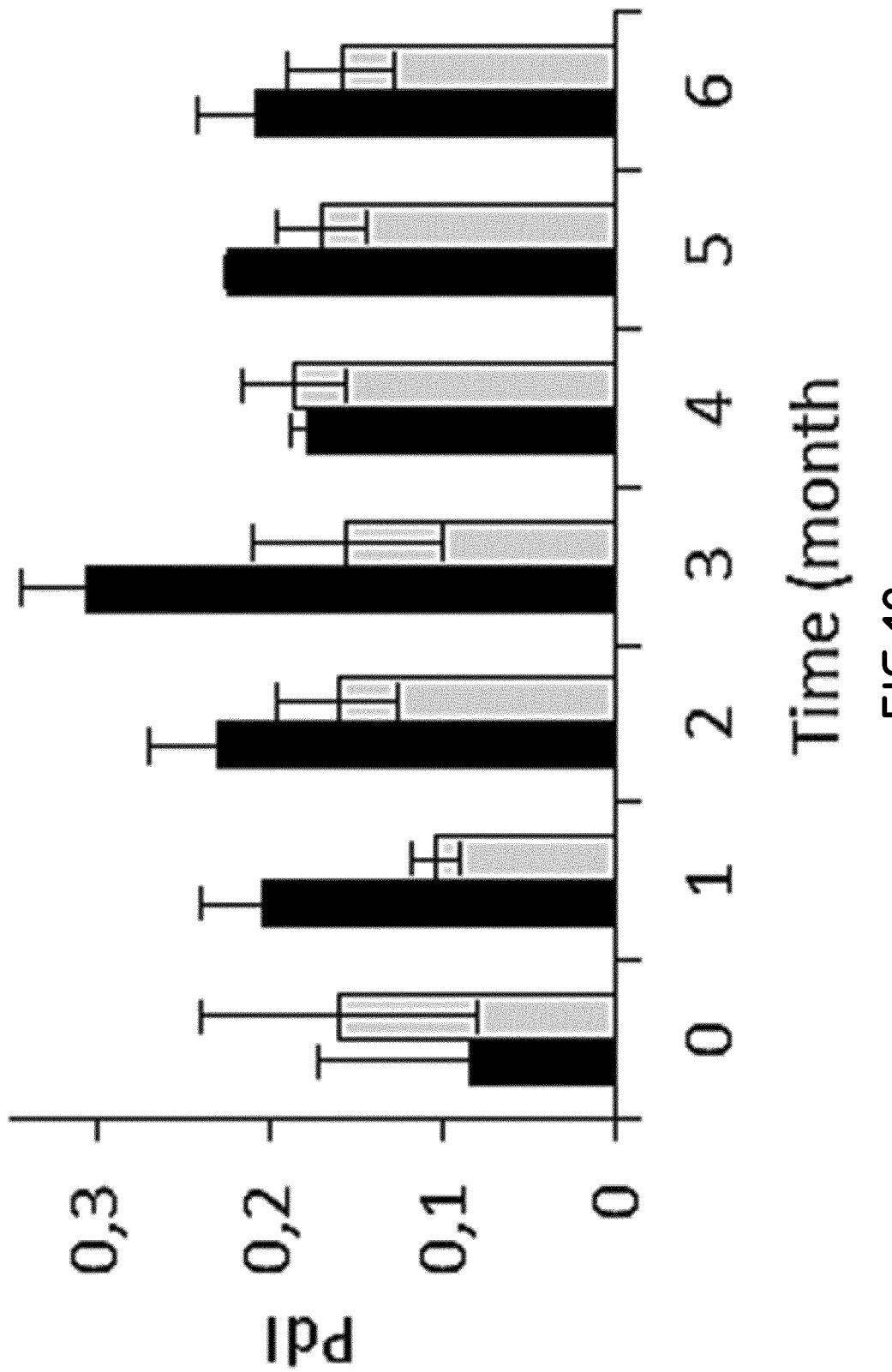

After these rheological measurements, the hydrogels were recovered, then dissolved to obtain LNC suspensions. The hydrodynamic diameter: Z-average (Z-ave), and polydispersity index (PdI) of LNCs were determined by dynamic light scattering on a Zetasizer® Nano ZS (Malvern Instruments S.A., Worcestershire, United Kingdom). The helium-neon laser, 4 mW, was operated at 633 nm, with the scattering angle fixed at 173° and the temperature at 25° C. The curve fittings of the correlation functions were performed using an exponential fit (Cumulant approach) for Z-Ave and PdI determinations of the LNCs in suspension.

d) Results:

No significant change for the appearance of the hydrogels (macroscopic observation) was observed. The values for the elastic G' and viscous G" moduli were constant whatever the diameters of the LNCs, up to 6 months (FIG. 10). The ratios G"/G' were comprised between 0.23 and 0.43, confirming a low value for the phase angle between the shear strain and the shear stress responses (between 13 and 23°). The elasticity of the hydrogels were preserved over 6-month storage at 4° C. Both Z-average and PdI values of LNCs showed significant increases from the first month (FIGS. 11 and 12). These variations can be due to a modification of the LNCs by conventional processes for the emulsion destabilization (coalescence or flocculation for examples), or to partial re-suspension to unique LNCs during the dissolution step of the hydrogels (presence of LNC aggregates).

Example 6: Extrusion of the Hydrogels Using Needles c) Method:

Hydrogels of LNCs (diameters of 50, 75 and 100 nm), loaded with Cyt-C16 2.5% (w/w$_{Labrafac}$) were formulated and put in 5-mL plastic syringe (SOFT-JECT®, HSW, Tuttlingen, Germany) prior completed gelation. The syringes were stored horizontally overnight at 4° C. to allow completed gelation.

Figure 13:
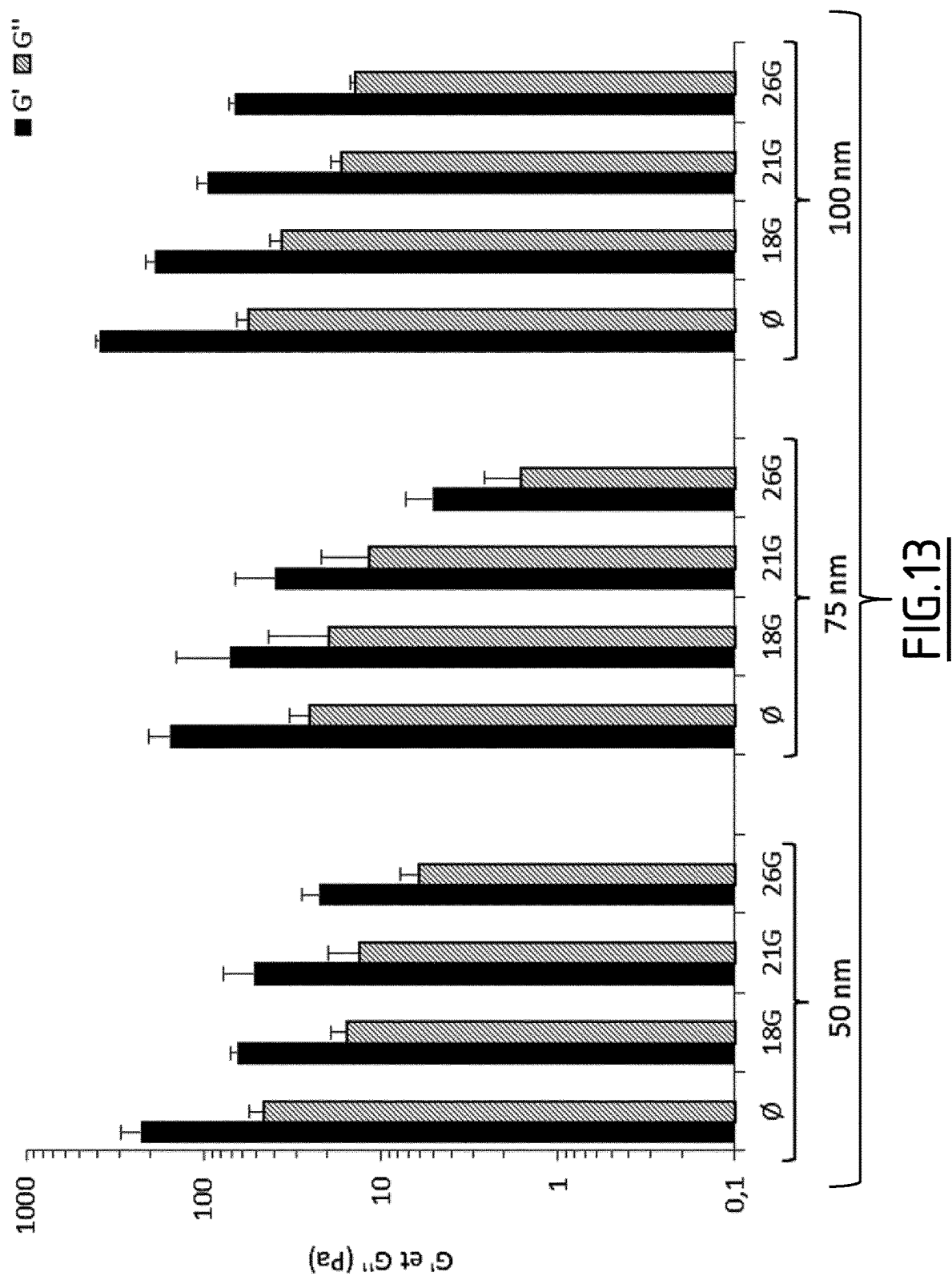
FIG. 13: Elastic G' (black bar) and viscous G" (hatched bar) moduli for the hydrogels of LNCs after their extrusion through needles (18, 21 et 26 G) compared to the non-extruded hydrogels of LNCs (Ø). Oscillation frequency: 1 Hz and shear strain: 0.1%. LNC diameter (nm)/LNC concentration (mg·mL$^{-1}$) for the hydrogels: 50/410.2; 75/561.6; and 100/503.8, loaded with Cyt-C16 2.5% (w/w$_{Labrafac}$) (n=3, mean±SD).

The viscoelastic properties of the hydrogels of LNCs at 25° C. were measured using a Kinexus® rheometer (Malvern Instruments S.A., United Kingdom), with a cone plate geometry (diameter 40 mm, angle: 2°). The hydrogels were deposited directly on the plate geometry of the rheometer, after extrusion through needles (Terumo Europe, Leuven, Belgium), and the cone geometry was placed in contact with the sample. Different needle sizes were tested: 18, 21 and 26 gauges (G), corresponding respectively to internal diameters of the needle of 1.2, 0.8 and 0.45 mm. Oscillatory strain sweeps at 1 Hz constant frequency were performed to determine the linear regime characterized by constant dynamic moduli (elastic: G' and viscous: G" moduli), independent of the strain amplitude. In this regime (0.1% constant strain), G' and G' were measured as a function of angular frequency (0.1 to 10 Hz). All these experiments were repeated in triplicate.

d) Results:

After extrusion through needles, both G' and G" values decreased while preserving the elastic property of the hydrogel (FIG. 13). Indeed, the ratio G"/G' after extrusion were comprised between 0.18 and 0.32, which corresponds to low values of phase angle between the shear strain and the shear stress responses (between 10 and 18°), whatever the LNC size forming the hydrogel. Without extrusion, the ratio G"/G' were comprised between 0.14 and 0.20, which corresponds to comparable phase angle (between 8 and 12°), whatever the LNC size forming the hydrogel. The main character of the viscoelastic properties of the hydrogels remains "solid" (the gel state) after their extrusion through the needles, and the rheological liquid state is never reached. The hydrogels are subjected to more shear stress with the thinnest needles, leading to lower G' and G" values.

Example 7: LNC Release from the Hydrogels c) Method:

The release study was performed using two hydrogels of LNCs (diameters: 50 and 100 nm, loaded with Cyt-C16 2.5% (w/w$_{Labrafac}$) and Nile Red (NR) 0.1% (w/w$_{Labrafac}$) in triplicate. During the formulation protocol of the hydrogels, the NR was first solubilized in Labrafac, before to process to the phase inversion method. At the end of the formulation protocol and prior the gelation, the formulations (300 µL) were carefully deposited in the bottom of a glass hemolysis tube (right edge, round bottom, 6 mL, NAFVSM, Andeville, France). The hydrogels were stored overnight at 4° C. to allow completed gelation. Then a volume of 5.7 mL of artificial extracellular matrix solution (HA 1 mg/mL, NaCl 6.4 mg/mL, MgCl$_2$·6H$_2$O 0.09 mg/mL, KCl 0.4 mg/mL, CaCl$_2$) 0.1 mg/mL, NaHCO$_3$ 2.1 mg/mL, pH=7.4, 37° C.) was carefully added to the top of the hydrogels, without modifying their shape. The tubes are then sealed and stored in the dark at 37° C.

200 µL of supernatant were collected at fixed time intervals, and replaced by 200 µL of fresh medium (at 37° C.). The collected samples were placed in a 96-well plate (Greiner bio-one GmbH, Frickenhausen, Allemagne). The fluorescence intensities were measured with a Fluoroscan Ascent® plate reader (Labsystems SA, Cergy-Pontoise, France), with excitation and emission wavelengths set at 515 and 590 nm, respectively. The release of LNCs was monitored over a 13-day period. The cumulative release profiles of the LNCs are obtained, considering that the 100% release corresponds to the fluorescence intensity value obtained for the complete dissolution of the hydrogels. The NR fluorescence intensity values are proportional to the NR concentration (encapsulated in the LNCs) in the entire range of concentrations considered in the study. Thus, the fluorescence intensity of the samples was measured without further dilution.

d) Results:

The complete dissolution of the hydrogels in the medium led to concentrations of LNCs close to 20 mg·mL$^{-1}$, and the release study was carried out under conditions which allow the complete release of the LNCs, i.e. the complete dissolution of the hydrogel.

Figure 14:
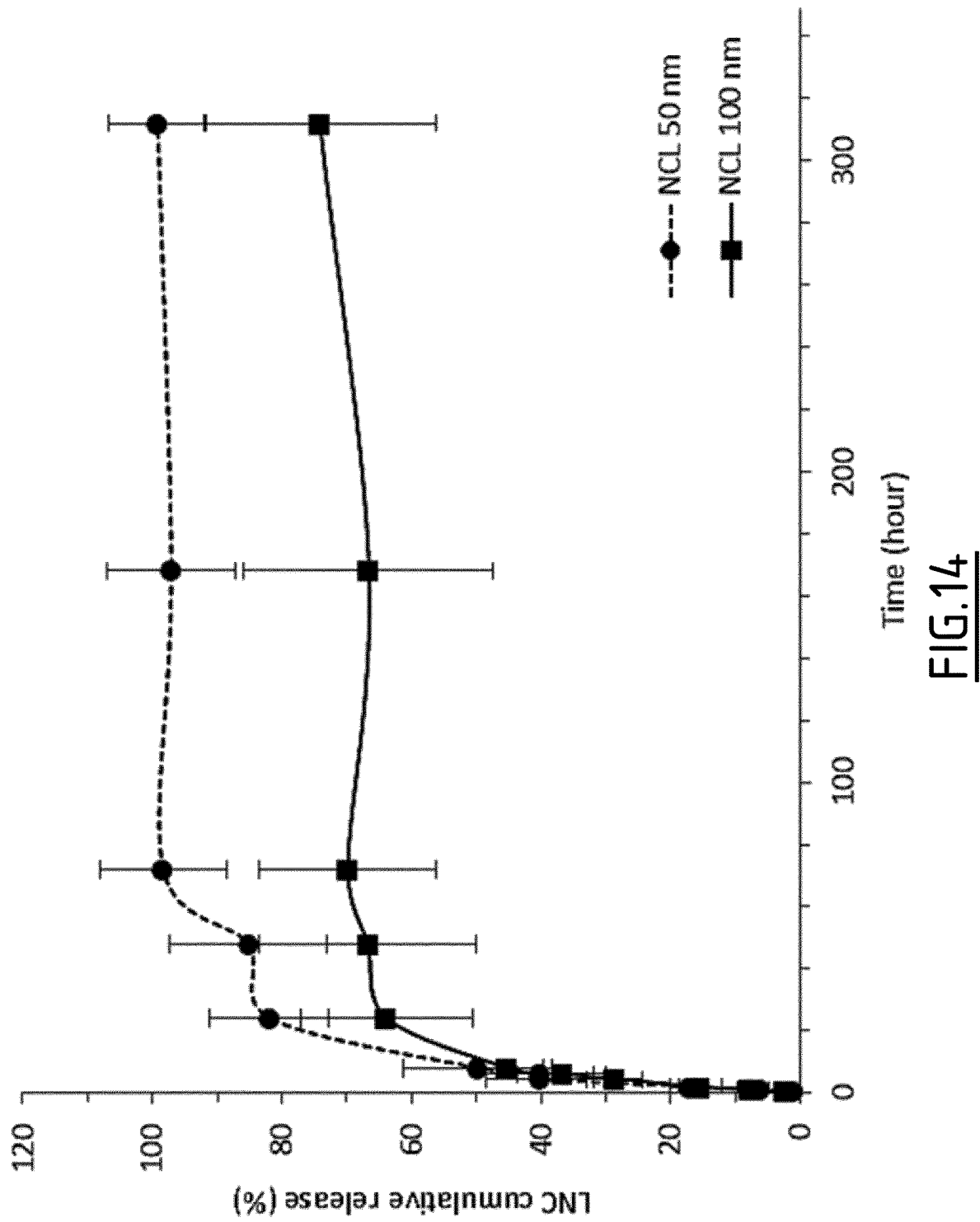
FIG. 14: LNC cumulative release from the hydrogels to an artificial extracellular matrix (pH=7.4, 37° C.). LNC diameter (nm)/LNC concentration (mg·mL$^{-1}$) for the hydrogels: 50/410.2; and 100/503.8, loaded with Cyt-C16 2.5% (w/w$_{Labrafac}$) and Nile Red 0.1% (w/w$_{Labrafac}$) (n=3, mean±SD).

During the first 24 hours, the LNCs were rapidly released. Proportions of 80 and 60% of LNCs were released from the hydrogels of LNC diameters of 50 and 100 nm, respectively. Over the next three days, the release gradually increased until reaching the maximum values of 95 and 70%. These values then remain constant for the next 10 days (FIG. 14). The LNCs with a diameter of 100 nm appeared to have a slightly slower release compared to the 50-nm diameter LNCs. Using LNC suspension controls (without Cyt-C16), the releases of LNCs reached a value of 100% after 1 hour, whatever the LNC size (results not shown).

Example 8: Cellular Toxicity c) Method:

THP-1 cells (human monocyte/macrophage cell line obtained from ATCC, Manassas, VA, USA) were grown in suspension at 37° C., 90% humidity, 5% CO2 in RPMI 1640 medium, completed with decomplemented FBS (10% v/v), penicillin (100 UI·mL$^{-1}$), streptomycin (100 mg·mL$^{-1}$), amphotericin B (0.25 mg·mL$^{-1}$), HEPES 10 mM (1% v/v), Pyruvate Sodium 100 mM (1% v/v) and β-mercaptoethanol 20 µM (1% v/v). Cell differentiation was induced in the same medium by adding PMA 200 nM. A 48-h incubation allows the cells to adhere (15·10$^3$ cells/well in a 96-well cell culture dish). After medium aspiration to eliminate non-adhered cells, cells were washed again with fresh medium.

Figure 15:
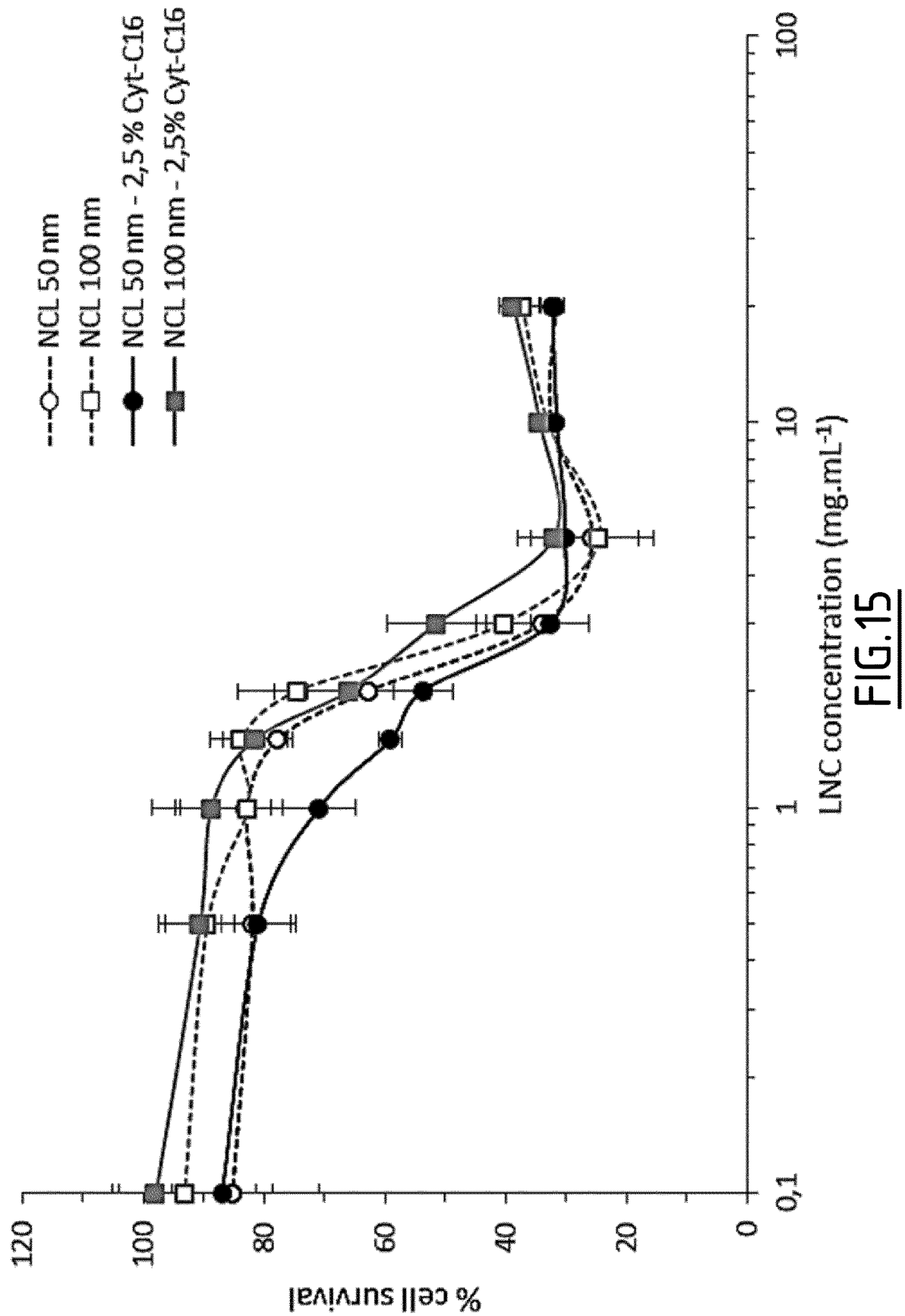
FIGS. 15 and 16: Living cell proportion: THP1 (FIG. 15) and B6-KPC3 (FIG. 16) cell lines vs LNC concentration after 48-h incubation at 37° C. LNC diameter: 50 (○●) and 100 nm (□■), loaded with Cyt-C16 0 (○□) or 2.5% (w/w$_{Labrafac}$) (●■). (n=3, mean±SD).
Figure 16:
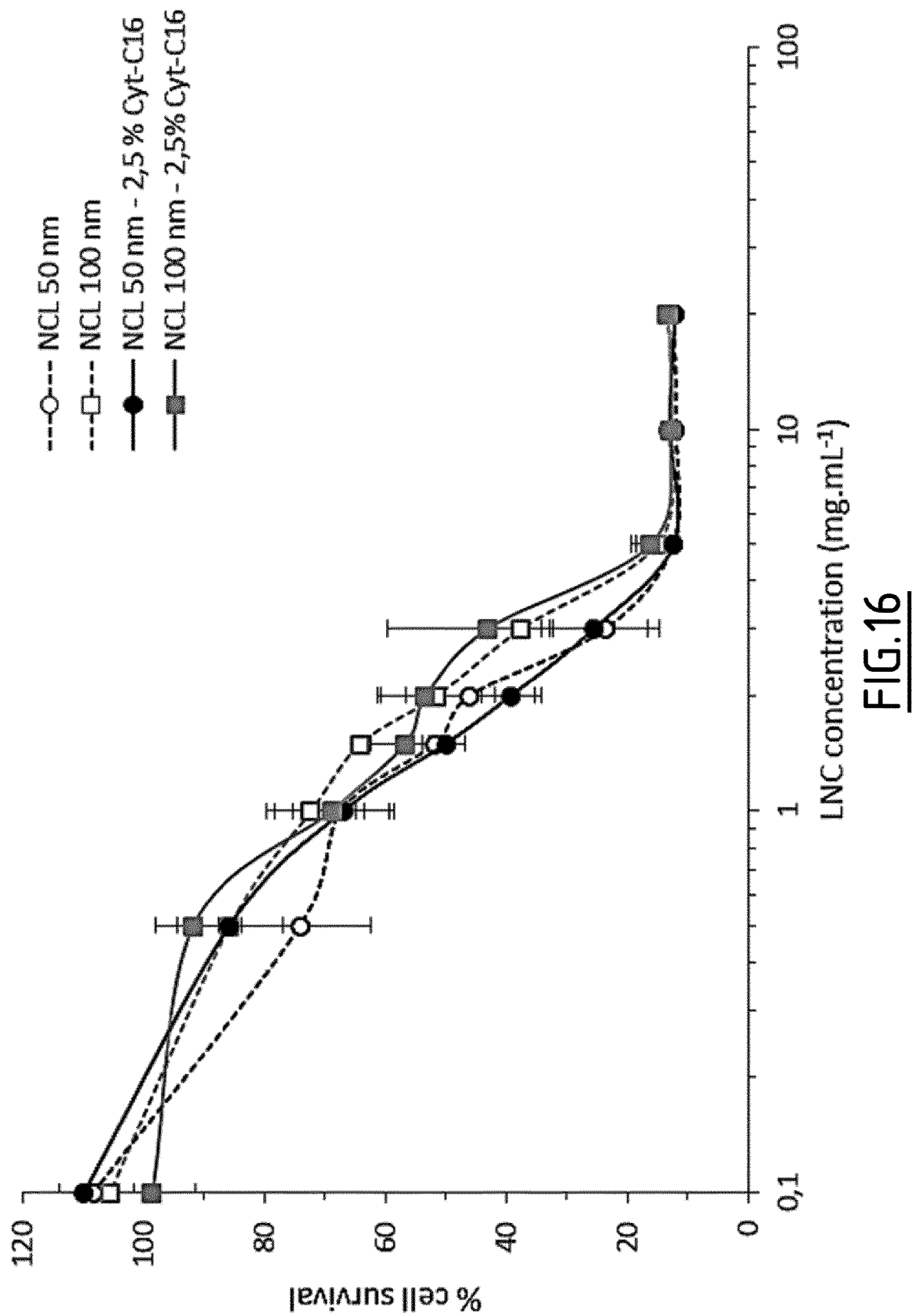

B6-KPC3 cells (pancreas tumor from transgenic KPC mice) (gift from the *Department of Oncology and Surgical Sciences of Padova*, Pr. Vincenzo Bronte), were grown in suspension at 37° C., 90% humidity, 5% CO2 in DMEM medium, completed with decomplemented FBS (10% v/v), penicillin (100 UI·mL$^{-1}$), streptomycin (100 mg·mL$^{-1}$), amphotericin B (0.25 mg·mL$^{-1}$), HEPES 10 mM (1% v/v), L-glutamin 2 mM (1% v/v), and β-mercaptoethanol 20 µM (1% v/v). The cells (3.5·10$^3$ cells/well in 200-µL medium) were then plated on a 96-well cell culture dish and left to grow for 48 h at 37° C. The cytotoxicitiy of diluted LNCs (diameter 50 or 100 nm), non-loaded or loaded with Cyt-C16 2.5% (w/w$_{Labrafac}$), in cell culture medium, was determined. Fresh cell culture medium was used as controls. Various amounts of LNCs (from 0.1 to 20 mg·mL$^{-1}$) were added into the wells and were incubated with the cells for 48 h. The number of living cells was determined using a MTS (3-(4,5-dimethylthiazol-2-yl)-5-(3-carboxymethoxyphenyl)-2-(4-sulfophenyl)-2H-tetrazolium salt) assay (colorimetric assay based on the conversion of a tetrazolium salt into formazan). Formazan absorbance was measured at 492 nm and 750 nm, directly from well plates using a spectrophotometer Multiscan Ascent® MP reader (Thermo Scientific, Courtaboeuf, France), after exposition to MTS (20 μL per well) for 2.5 h at 37° C. The percentage of cell viability was calculated according to the following equation:

$$\text{Alive cells (\%)} = \frac{\text{Abs }(T)}{\text{Abs }(C)} \times 100$$

with Abs (T) and Abs (C), the absorbance values of cells incubated with LNCs and cells incubated with fresh medium (control), respectively. The quantity of formazan is proportional to the number of living cells in the culture. The relative percentage of living cells (compared to living cells with fresh medium control) was reported as the mean±SD of three different experiments. The IC50 values (half maximal inhibitory LNC concentrations) were assessed.

d) Results:

Whatever their diameter, the LNCs had a similar cytotoxic activity on the two cell lines depending on their concentrations (FIGS. 15 and 16). For 50-nm diameter NCLs, 1050 values (mean±SD) were estimated at 2.13±0.30 and 1.66±0.23 mg·mL$^{-1}$ for the THP1 and B6-KPC3 cell lines, respectively. For 100-nm diameter LNCs, these values were estimated at 2.51±0.36 and 2.12±0.24 mg·mL$^{-1}$, for the same cell lines, respectively.

The addition of Cyt-C16 at the LNC surface (2.5% (w/w$_{Labrafac}$)) did not significantly modify the IC50 values. For 50-nm diameter Cyt-C16-loaded LNCs, 1050 values were estimated at 2.15±0.19 and 1.47±0.21 mg·mL$^{-1}$ for the THP1 and B6-KPC3 cell lines, respectively. For 100-nm diameter Cyt-C16-loaded LNCs, IC50 values were estimated at 3.08±0.50 and 2.16±0.25 mg·mL$^{-1}$, for the same cell lines, respectively.

Cyt-C16, the synthesized crosslinking agent, does not cause additional cytotoxicity in comparison to native LNCs, regarding these 2 cell lines.

Example 9: In Vivo Tolerability c) Method:

All the animal experiments were performed in agreement with the EEC guidelines and the "Principles of Laboratory Animal Care" (NIH Publication No. 86-23, revised 1985) and with the agreement of Comité d'Ethique pour l'Expérimentation Animale des Pays-de-la-Loire (authorization CEEA 2012-37 et 2012-73). Female rats (Sprague-Dawley) (8-week old) were raised, housed and maintained at the Angers University animal facility (SCAHU) under controlled conditions (12-h light/dark schedule, 24° C., tap water and chow provided ad libitum) during all the study. The weight, the general appearance and the behavior of the rats were daily monitored.

57 rats were randomly divided into 4 groups (no administration (n=3); hydrogel of LNCs (diameter: 50 nm, loaded with Cyt-C16 2.5% (w/w$_{Labrafac}$), LNC concentration: 410.2 mg·mL$^{-1}$) (n=18); oleogel (Cyt-C16 1% (w/w$_{Labrafac}$)) (n=18); and sesame oil (control, approved for subcutaneously and intramuscularly administered drug formulations) (n=18)), which were sacrificed at different time points (n=3 per time point per group). The rats received a single subcutaneous injection of the appropriate formulation (500 μL, 18-G needle) in the shaved higher dorsal area under isoflurane anesthesia (5%, oxygen flow 3 L/min) (Isoflurane Belamont, Belamont Laboratoires, Boulogne-Billancourt, France). After the injection, the needle was held in place for 10 s to prevent the leakage of the implant from the injection site.

At the different time points (1, 2, 4, 7, 14 and 28 days), the rats were once again anesthetized under isoflurane, sacrificed by cardiac puncture and the tissues adjacent to the injection site and the remaining implants (3×3 cm pieces) were collected and fixed with 10% neutral-buffered formalin. 500-μL volume of collected blood was put into EDTA-K2 vials (Microtainer® MAP K2 EDTA, BD, New Jersey, Etats-Unis) and store at 4° C. for the hematologic profile analyses. Additional 500-μL volume of collected blood was put into vials containing heparin (Li-Heparin—Tube Micro, Sarstedt, Marnay, France), centrifuged (15 min, 2000 g, 4° C.). About 200 μL of plasma were recovered and stored at −20° C. for biochemical profile analyses.

Hematologic and biochemical profiles were characterized at the University Hospital of Angers (Pr. Marc Zandecki and Dr. Valérie Moal, respectively) using standard protocols. Studied parameters were:

iii) erythrocyte concentration, hemoglobin concentration, hematocrite, mean corpuscular volume, mean corpuscular hemoglobin, mean corpuscular hemoglobin concentration, platelet concentration, mean platelet volume, leucocyte concentration and leukocyte count, for hematologic profile analyses; and iv) urea, sodium, potassium, chloride, creatinine, alkaline phosphatase, aspartate aminotransferase and alanine aminotransferase concentrations, for the biochemical profile analyses.

The tissues adjacent to the injection site were processed and embedded in paraffin. Glass slides with 5-μm tissue sections were prepared using a Leica 2155 microtome (Leica Microsystems Inc., Richmond Hill, ON, Canada). Slides of each implant were stained according to a hematoxylin-eosin standard protocol of University Hospital of Angers (Pr. Marie-Christine Rousselet). The slides were observed using a Scanscope® CS System scanner (Aperio Technologies, Leica Biosystems Imaging, Wetzlar, Allemagne) to obtain high resolution pictures. The local inflammatory response was assessed by histological evaluation of the surrounding tissue for signs of acute inflammation (neutrophils and eosinophils) and chronic inflammation (histocytes, plasmocytes, lymphocytes, multinucleated giant cells, fibroblasts, neo-angiogenesis, and collagen deposition). The intensity of the response was graded on a scale from normal (0), minimal (+/−), mild (+), moderate (++), and severe (+++), depending on the number of cells and the general appearance of the tissues.

d) Results:

The subcutaneous administration of the three formulations did not pose any problem. The hydrogel of LNCs and the oleogel, due to their viscoelastic properties, were well retained inside the subcutaneous site. Only during the first 24 hours after administration, whatever the formulation, scratching and grooming behaviors of the injection site were observed in the rats. Up to the end of the study, no animal showed any change in behavior (decrease in grooming, asthenia) or signs of suffering, and the weight of the rats, frequently monitored, presented a normal evolution. Moreover, the injected formulations remained visible under the skin, and the area surrounding the injection site does not appear to be infected, erythematous or painful, throughout the study. Only 2 rats receiving the oleogel had a crust at the site of injection.

Whatever the formulation and the time considered, the hematological and biochemical profiles were not significantly modified. Between day 2 and day 14, the overall number of leucocytes slightly increased but remained close to the normal value, with a distribution of the different types of leukocytes unchanged and comparable to the normality during the 28 days (data not shown).

Figure 17:
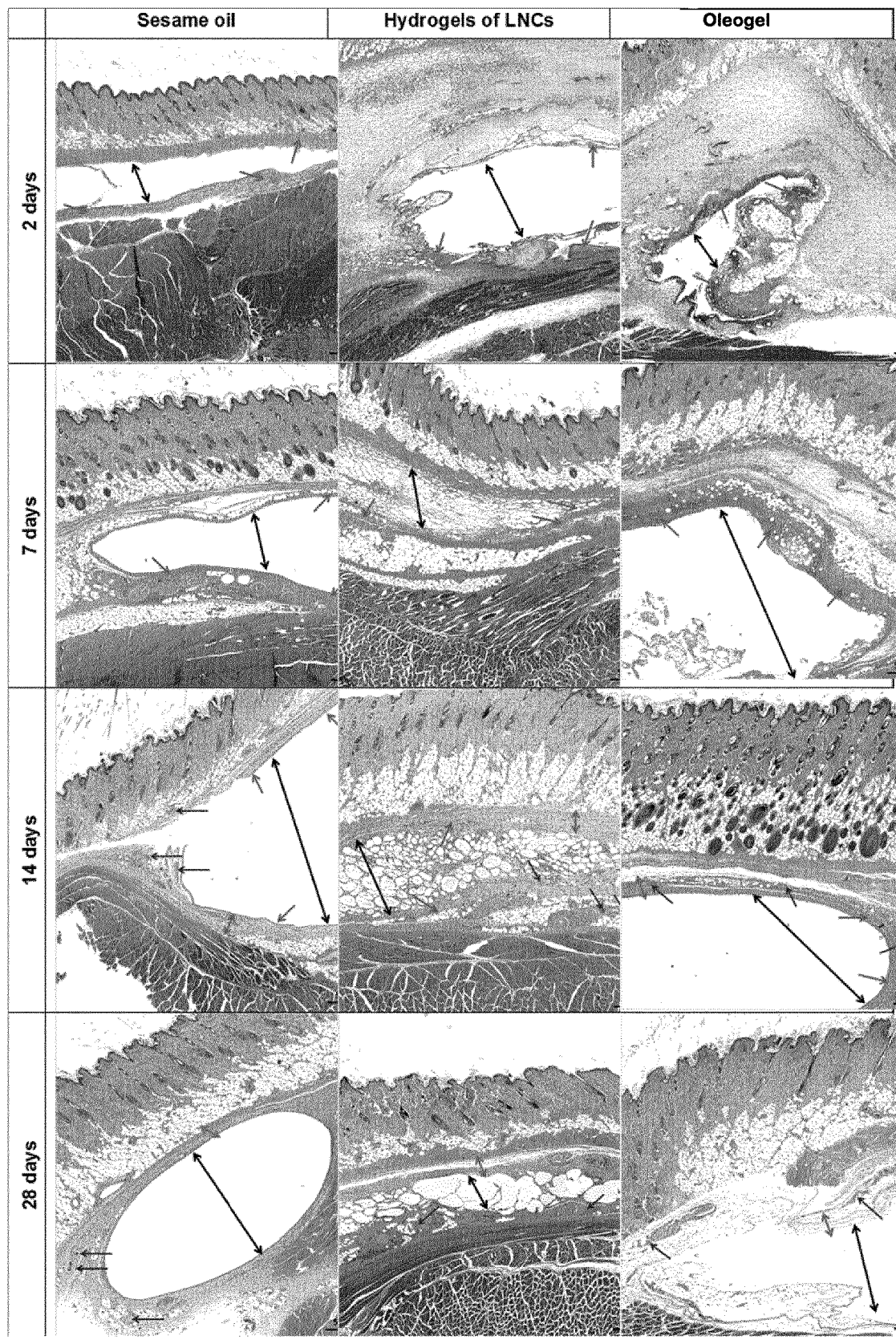
FIG. 17: Representative microscopic sections of the subcutaneous tissues surrounding the 500-μL volume implants: hydrogel of LNCs (diameter: 50 nm, loaded with Cyt-C16 2.5% (w/w$_{Labrafac}$), and LNC concentration of 410.2 mg·mL$^{-1}$); oleogel (Cyt-C16 1% (w/w$_{Labrafac}$)); and sesame oil; 2, 7, 14 and 28-day post-subcutaneous administration in female rats (Sprague-Dawley).

Representative pictures for histological analysis are reported in FIG. 17. In the first 24 hours, a similar acute inflammatory response was observed for the 3 implants. The inflammatory response resulted in the recruitment of numerous leukocytes (neutrophils, granulocytes and some eosinophilic granulocytes) all around the site of injection, and more concentrated at the margin of the implant cavities. In addition, interstitial edemas were present, appearing to be slightly more important for the gel formulations. After 48 hours, the recruitment of the granulocytes increased around the well delimited cavity of the implants, and stabilized at day 4, with apparition of fibroblasts.

After one week, the granulocytes began to decrease and were replaced by macrophages. In addition, the fibroblasts increased. The cavity of the oleogel and sesame oil implants remained with the well-defined appearance, while the cavities for the hydrogel of LNCs broke up into several large vacuoles with infiltration of living tissues.

At day 14, the cavities containing the oleogel and the sesame oil implant were always well visible while cavities containing the hydrogels of LNCs had an increasingly infiltrated appearance (extracellular matrix and some cells). The empty cavities were now surrounded by a fibrous capsule composed of fibroblasts and collagen deposits. Some leukocytes, mainly mononuclear cells (macrophages and lymphocytes), were still found inside and around this capsule but their number remained moderate. In addition, neo-angiogenesis was observed all around the implant. Finally, after 28 days, the cavities containing the oleogel and the sesame oil implants were always well visible and those for hydrogels of LNCs had a more fragmented and infiltrated appearance by living tissues. They are surrounded by a fibrous capsule.

In summary, during the week following their injection, implants based on hydrogels of LNCs and oleogels, induced an initial phase of acute inflammation followed by a subchronic/chronic phase (see table 4 and FIG. 17). This evolution and the development of a consequent fibrosis around the implants is classical of the inflammatory responses of the foreign body reaction type. This local inflammatory response was not associated with serious symptoms. The trauma induced by the use of needles during the injection could have also contributed to the initiation of the acute inflammation. In addition, the control based on sesame oil caused the same inflammatory response. This last is an excipient currently used and approved for parenteral administration. Thus, the inflammatory responses caused by the two gel platforms are acceptable.

TABLE 4 inflammatory response of the subcutaneous tissues surrounding the 500-μL volume implants: hydrogel of LNCs (diameter: 50 nm, loaded with Cyt-C16 2.5% (w/w$_{Labrafac}$), and LNC concentration of 410.2 mg · mL$^{-1}$); oleogel (Cyt-C16 1% (w/w$_{Labrafac}$)); and sesame oil, 1 to 28-day post-subcutaneous administration to female rats (Sprague-Dawley). (n = 3).

|  |  | Leucocyte infiltration | Fibroblasts et collagen deposit | Neo-angiogenesis |
|---|---|---|---|---|
| 1 day | Sesame oil | +++ | 0 | 0 |
|  | Hydrogel of LNCs | +++ | 0 | 0 |
|  | Oleogel | +++ | 0 | 0 |
| 2 days | Sesame oil | +++ | 0 | 0 |
|  | Hydrogel of LNCs | +++ | 0 | 0 |
|  | Oleogel | +++ | 0 | 0 |
| 4 days | Sesame oil | +++ | +/− | +/− |
|  | Hydrogel of LNCs | +++ | +/− | 0 |
|  | Oleogel | +++ | + | +/− |
| 7 days | Sesame oil | ++ | ++ | + |
|  | Hydrogel of LNCs | ++ | ++ | + |
|  | Oleogel | ++ | ++ | + |
| 14 days | Sesame oil | + | +++ | ++ |
|  | Hydrogel of LNCs | + | +++ | +++ |
|  | Oleogel | + | +++ | ++ |
| 28 days | Sesame oil | +/− | +++ | ++ |
|  | Hydrogel of LNCs | +/− | +++ | +++ |
|  | Oleogel | +/− | +++ | ++ |

0: normal,
+/−: minimal,
+: mild,
++: moderate and
+++: severe

The invention claimed is:

1. A method for treating and/or preventing vascular disease, comprising administering to a mammal in need thereof a therapeutically effective amount of an hydrogel or an oleogel,
wherein said hydrogel comprises nanocapsules, an aqueous phase, and an active ingredient N in an aqueous phase of the hydrogel, said hydrogel having a G"/G' inferior to 1, and said nanocapsules comprise at least one compound A and have a mean size diameter of less than 150 nm,
wherein said oleogel comprises at least one compound A an oily phase, and an active ingredient P in the oily phase of the oleogel, said oleogel having a G"/G' ratio inferior to 1,
and wherein said compound A has the following formula (A):

wherein:
B is selected from the group consisting of a nucleobase, a nucleoside, a deoxynucleoside, and one of their derivatives, and
R is a linear or branched, saturated or unsaturated ($C_9$-$C_{21}$) alkyl, said alkyl being optionally substituted by one or more substituent(s) selected from the group consisting of:
—COOH, —OH, —SH, —NH$_2$, —COORa, —ORa, —SRa, and —NRaRb,
with Ra being a linear or branched, saturated or unsaturated ($C_1$-$C_{10}$) alkyl, and Rb being H or a linear or branched, saturated or unsaturated ($C_1$-$C_{10}$) alkyl, provided that said compound A is not:

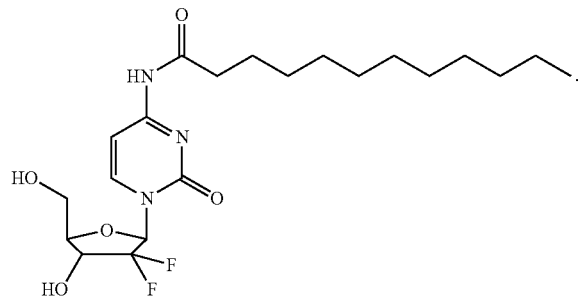 [SMILES: CCCCCCCCCCCC(=O)Nc1ccn(C2OC(CO)C(O)C2(F)F)c(=O)n1]

2. The method of claim 1, wherein compound A has a formula selected from the group consisting of:

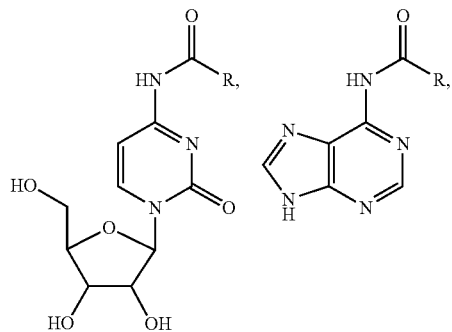

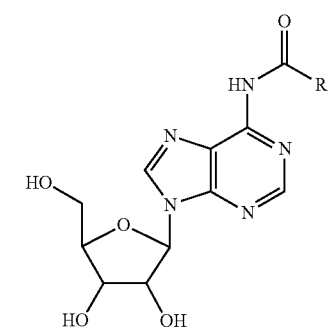

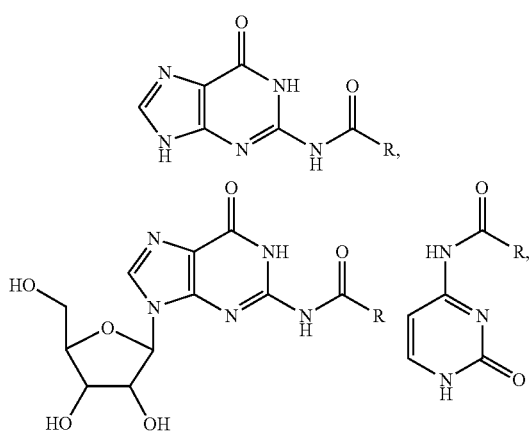

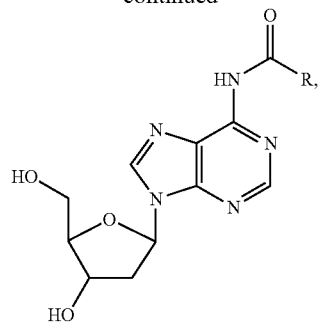

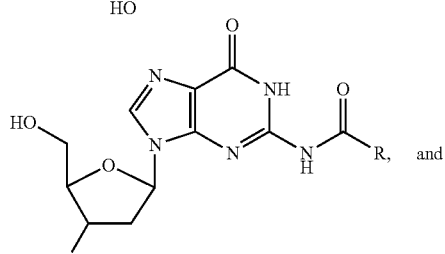

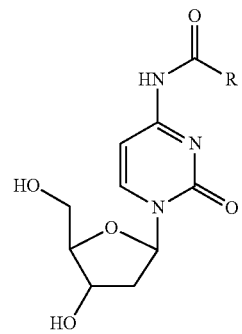

with R being as defined in claim 1.

3. The method of claim 1, wherein said hydrogel or oleogel is administered locally.

4. The method of claim 1, wherein said hydrogel or oleogel is a sustained release drug delivery system.

5. The method of claim 1, wherein the vascular disease is vascular hyperplasia.

6. The method of claim 1, wherein the vascular disease is intimal hyperplasia.

7. The method of claim 6, wherein administration to a mammal in need thereof of the therapeutically effective amount of the hydrogel or the oleogel follows or replaces stent implantation.

8. A method for treating and/or preventing cancer, comprising administering to a mammal in need thereof a therapeutically effective amount of a hydrogel or an oleogel after resection of a solid tumor or by intratumoral administration, wherein said hydrogel comprises nanocapsules, an aqueous phase, and an active ingredient N in the aqueous phase of the hydrogel, said hydrogel having a G"/G' inferior to 1, and said nanocapsules comprises at least one compound A and have a mean size diameter of less than 150 nm, wherein said oleogel comprises at least one compound A, an oily phase, and an active ingredient P in the oily phase of the oleogel, said oleogel having a G"/G' ratio inferior to 1, and wherein said compound A has the following formula (A):

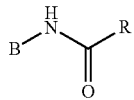
(A)

wherein:
- B is selected from the group consisting of a nucleobase, a nucleoside, a deoxynucleoside, and one of their derivatives, and
- R is a linear or branched, saturated or unsaturated ($C_9$-$C_{21}$) alkyl, said alkyl being optionally substituted by one or more substituent(s) selected from the group consisting of:
  —COOH, —OH, —SH, —NH$_2$, —COORa, —ORa, —SRa, and —NRaRb,
- with Ra being a linear or branched, saturated or unsaturated ($C_1$-$C_{10}$) alkyl, and Rb being H or a linear or branched, saturated or unsaturated ($C_1$-$C_{10}$) alkyl,
- provided that said compound A is not:

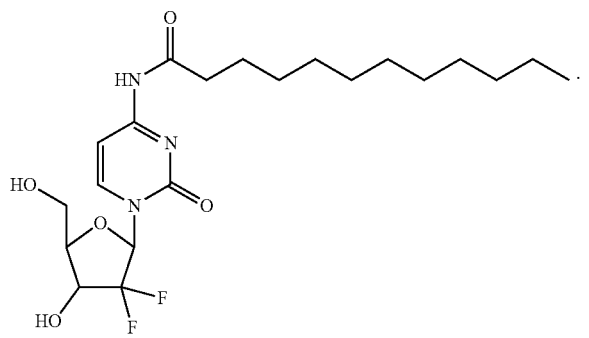 [SMILES: CCCCCCCCCCCC(=O)Nc1ccn(C2OC(CO)C(O)C2(F)F)c(=O)n1]

9. The method of claim 8, wherein compound A has a formula selected from the group consisting of:

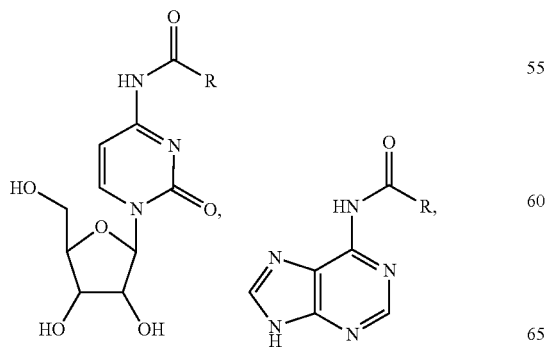

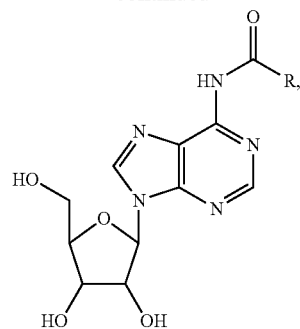

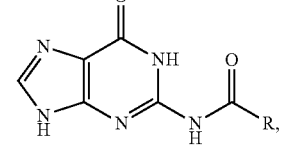

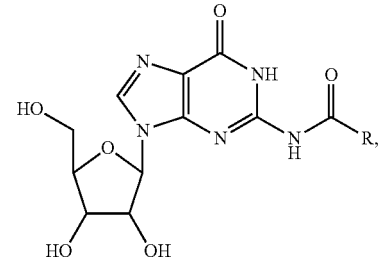

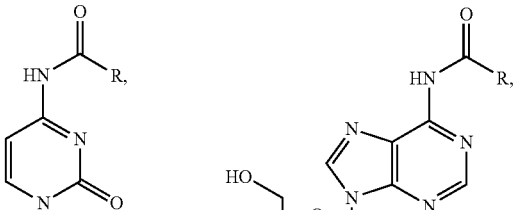

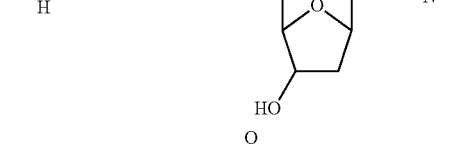

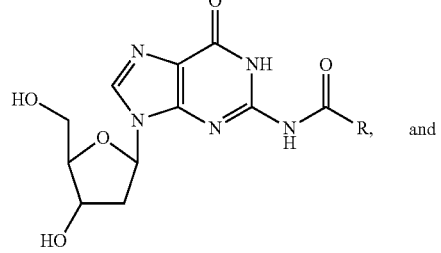
and

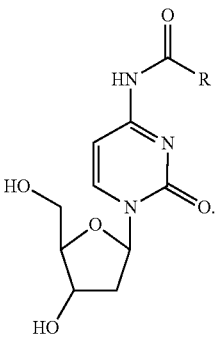

10. The method of claim 8, wherein said hydrogel or oleogel is administered locally.

11. The method of claim 8, wherein said hydrogel or oleogel is a sustained release drug delivery system.

\* \* \* \* \*